United States Patent [19]

Boyd et al.

[11] Patent Number: 5,578,626
[45] Date of Patent: Nov. 26, 1996

[54] PHARMACEUTICAL COMPOSITIONS

[75] Inventors: Edward A. Boyd, Purley; Brenda Costall, Addingham; Mary E. Kelly, Thornton; Philip J. Parsons, Reading, all of England

[73] Assignee: British Technology Group Limited, London, England

[21] Appl. No.: 478,142

[22] Filed: Jun. 7, 1995

Related U.S. Application Data

[62] Division of Ser. No. 290,752, Aug. 15, 1994, Pat. No. 5,476,867.

[30] Foreign Application Priority Data

Feb. 19, 1992 [GB] United Kingdom .................... 9203500
Jan. 19, 1993 [GB] United Kingdom .................... 9300921

[51] Int. Cl.$^6$ ...................................................... A61K 31/42
[52] U.S. Cl. .............................................................. 514/379
[58] Field of Search .............................................. 514/379

[56] References Cited

U.S. PATENT DOCUMENTS

| 4,452,799 | 6/1984 | Temple et al. ............................ 424/250 |
| 5,049,564 | 9/1991 | DeBernardis et al. ................... 514/290 |
| 5,114,936 | 5/1992 | Wettlaufer et al. ....................... 548/241 |

FOREIGN PATENT DOCUMENTS 1540580  2/1979  United Kingdom .

OTHER PUBLICATIONS

I. Furukawa et al. "Direct synthesis of isoxazoline derivatives . . . " Chemical Abstracts #159012v, 1991, 115, p. 926.
F. A. Lakhvich et al. "Reductive cleavage of 4,5–cycloalkanoisoxazolines", Chemical Abstracts#135125e, 1989, 110, p. 705.
D. P. Curran et al. ". . . Regio and Stereoselective Exo Alkylation. . . " Journal of the American Chemical Society, 1987, 109, pp. 3036–3040.
D. P. Curran "Reduction of $\Delta^2$–Isoxazolines . . . ", Journal of the American Chemical Society,1982, 104, pp. 4024–4026.
D. P. Curran et al. "Reduction of substituted $\Delta^2$–Isoxazolines . . . ", Journal Organic Chemistry, 1984, 49, pp. 3474–3478.
P. A. Wade et al., "Benzenesulfonylnitrile oxide . . . ", Journal of the American Chemical Society, 1979, 101, pp. 1319–1320.
G. Zinner et al. ". . . synthesis of 4,5–tetramethylene–$\Delta^2$–isoxazolines", Chemische Berichte, 1965, 98, pp. 1353–1354.
S. Mzengeza et al. "Dipolar cycloaddition reactions . . . "Journal of the Chemical Society, Chemical Communications 194. Letchworth, GB, pp. 606–607. 1984.
A. Vasella. "Stereoselektivitat und . . . " Helvetica Chimica Acta, vol. 60 No. 4, 1 Jun. 1966, Basel CH, pp. 1273–1295.
J. T. Bailey et al. "Annelation of cyclic dienes to amino . . . ."Journal of Organic Chemistry, vol. 47 No. 5, 26 Feb. 1982, Easton, US, pp. 857–863.

*Primary Examiner*—Allen J. Robinson
*Attorney, Agent, or Firm*—Nixon & Vanderhye

[57] ABSTRACT

Compounds of formula (I)

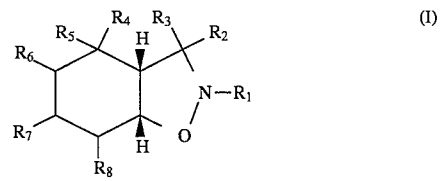

in which $R_1$ represents hydrogen, a $C_{1-6}$ aliphatic hydrocarbyl group or a $C_{1-4}$ aliphatic hydrocarbyl group substituted by a $C_{3-6}$ alicyclic hydrocarbyl group or by a phenyl group, which phenyl group is unsubstituted or substituted by a halogeno or $C_{1-3}$ halogenoalkyl group, $R_2$ represents hydrogen, $R_3$ represents hydrogen, a 5-or 6-membered ring aromatic heterocyclyl group containing one or two heteroatoms selected from nitrogen, oxygen and sulphur which is unsubstituted or substituted by a halogeno or $C_{1-3}$ halogenoalkyl group, or a group AR wherein A is a straight chain $C_{1-4}$ aliphatic hydrocarbyl group terminally substituted by R which is hydrogen, a phenyl group or a 5-or 6-membered ring aromatic heterocyclyl group containing one or two heteroatoms selected from nitrogen, oxygen and sulphur, which phenyl or heterocyclyl group R is unsubstituted or substituted by a halogeno or $C_{1-3}$ halogenoalkyl group, $R_4$ and $R_5$ each represent hydrogen or together represent an oxo group and $R_6$, $R_7$ and $R_8$ each represent hydrogen, or $R_4$ represents hydrogen and two of $R_5$, $R_6$, $R_7$ and $R_8$ together represent the second bond of a double bond joining positions 4 and 5, 5 and 6 or 6 and 7 with the remaining two of $R_5$, $R_6$, $R_7$ and $R_8$ representing hydrogen, the compound optionally being in the form of a salt thereof formed with a physiologically acceptable inorganic or organic acid, are of value for the treatment of anxiety and in the improvement of learning ability and/or the reversal of amnesia.

20 Claims, 16 Drawing Sheets n = 5.   *P<0.001 (ANXIOLYSIS).

n = 5.  † P < 0.001 (ANXIOGENESIS).  * P < 0.001 (ANXIOLYSIS).
° P < 0.001 (INHIBITION ANXIOGENESIS).
DIAZEPAM (DIAZ) 10mg/kg i.p. b.d. 7 DAYS AND WITHDRAWN (W/D) FOR 24h n = 5.   † P<0.001 (ANXIOGENESIS).   *P<0.001 (ANXIOLYSIS).
°P<0.001 (INHIBITION ANXIOGENESIS).
COCAINE (COC) 1mg/kg i.p. b.d. 14 DAYS AND WITHDRAWN (W/D) FOR 24h.

n = 5. *P<0.001 (IMPROVED 'LEARNING' AS COMPARED TO DAY 1).
† P<0.001 (SCOPOLAMINE IMPAIRMENT OF HABITUATION PATTERNS).

n = 5.  *P<0.001 (IMPROVED LEARNING AS COMPARED TO DAY 1).
° P<0.001 (INHIBITION OF SCOPOLAMINE IMPAIRMENT).
TESTING EACH DAY 40 MIN AFTER ADMINISTRATION OF SP 1640.

n = 5.  *P<0.05 – P<0.001 (IMPROVED HABITUATION AS COMPARED TO DAY 1)
°P<0.001 (INHIBITION OF SCOPOLAMINE IMPAIRMENT).

n = 5.   *P<0.001 (IMPROVED HABITUATION AS COMPARED TO DAY 1).

n = 5.

n = 5.
*P<0.01 – P<0.001 (IMPROVED HABITUATION AS COMPARED TO DAY 1).

PHARMACEUTICAL COMPOSITIONS

This is a Rule 60 Division of application Ser. No. 08/290,752, filed 15, Aug. 1994, U.S. Pat. No. 5,476,867.

This invention relates to psychoactive compounds of value in the treatment of anxiety and in the improvement of learning ability and the reversal of amnesia.

DESCRIPTION OF THE INVENTION

Accordingly the present invention comprises a compound of formula (I)

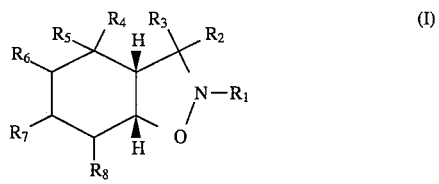

in which $R_1$ represents hydrogen, a $C_{1-6}$ aliphatic hydrocarbyl group or a $C_{1-4}$ aliphatic hydrocarbyl group substituted by a $C_{3-6}$ alicyclic hydrocarbyl group or by a phenyl group, which phenyl group is unsubstituted or substituted by a halogeno of $C_{1-3}$ halogenoalkyl group, $R_2$ represents hydrogen, $R_3$ represents hydrogen, a 5- or 6-membered ring aromatic heterocyclyl group containing one or two heteroatoms selected from nitrogen, oxygen and sulphur which is unsubstituted or substituted by a halogeno or $C_{1-3}$ halogenoalkyl group, or a group AR wherein A is a straight chain $C_{1-4}$ aliphatic hydrocarbyl group terminally substituted by R which is hydrogen, a phenyl group or a 5- or 6-membered ring aromatic heterocyclyl group containing one or two heteroatoms selected from nitrogen, oxygen and sulphur, which phenyl or heterocyclyl group R is unsubstituted or substituted by a halogeno or $C_{1-3}$ halogenoalkyl group, $R_4$ and $R_5$ each represent hydrogen or together represent an oxo group and $R_6$, $R_7$ and $R_8$ each represent hydrogen, or $R_4$ represents hydrogen and two of $R_5$, $R_6$, $R_7$ and $R_8$ together represent the second bond of a double bond joining positions 4 and 5, 5 and 6 or 6 and 7 with the remaining two of $R_5$, $R_6$, $R_7$ and $R_8$ representing hydrogen, the compound optionally being in the form of a salt thereof formed with a physiologically acceptable inorganic or organic acid, for use in therapy.

The invention further comprises the compounds per se of formula (I) as just defined with the exception of the compound in which each of $R_1$ to $R_8$ is hydrogen, which has been described by Vasella (Helvetica Chimica Acta, 1977, 60, 1273–1293) as a compound produced in an investigation of the reactions of N-alkoxyalkyl nitrones.

The system of numbering used herein is based on that of the benzo[d]isoxazole ring system as shown below

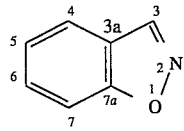

The standard method is used for indicating stereochemistry in formula (I), i.e. a thickened line represents a bond projecting upwardly from the plane of the paper. It will be seen that the compounds of the present invention therefore have cis stereochemistry with respect to the relative orientation of the hydrogen atoms at positions 3a and 7a.

The group $R_1$ may be hydrogen but, if this is the case, it is preferred that $R_3$ is other than hydrogen. However, $R_1$ is preferably a branched or especially straight chain substituted or especially unsubstituted aliphatic hydrocarbyl group. This monovalent aliphatic hydrocarbyl group may be unsaturated, especially by one double or triple bond, particularly when the group is unsubstituted, for example being a propargyl or especially an allyl group. Preferably, however, it is saturated, for example being a methyl, ethyl, n-propyl or isopropyl group with the straight chain alkyl groups and especially methyl being preferred, although with some particular interest in ethyl and larger groups when it is substituted, particularly by phenyl. Where $R_1$ is an aliphatic hydrocarbyl group substituted by an alicyclic hydrocarbyl group or less preferably an unsubstituted or substituted phenyl group, the substituent group is conveniently terminally substituted on the aliphatic hydrocarbyl group. The alicyclic hydrocarbyl group is preferably a cycloalkyl group such as cyclopropyl or cyclohexyl and the phenyl group is preferably unsubstituted although when it is substituted the preferences are as described hereinafter for substituted phenyl groups $R_3$. Examples of such substituted aliphatic hydrocarbyl groups $R_1$ are cyclohexylmethyl and especially cyclopropylmethyl, and also phenylmethyl and especially 2-phenylethyl.

The group $R_2$ is hydrogen. Although each of $R_4$ to $R_8$ may be hydrogen, the groups $R_4$ and $R_5$ are preferably either together an oxo group or $R_4$ is hydrogen and $R_5$ together with $R_6$ is the second bond of a double bond joining positions 4 and 5. Alternatively, when $R_4$ is hydrogen but $R_5$ and $R_6$ are not a bond, either $R_6$ and $R_7$ may be the second bond of a double bond joining positions 5 and 6 or $R_7$ and $R_8$ may be the second bond of a double bond joining positions 6 and 7. However, it is preferred that, where the one optional double bond in the six membered ring is present, it joins positions 4 and 5 so that $R_7$ and $R_8$ are usually each hydrogen.

A group $R_3$ which is hydrogen is of particular interest, especially when $R_4$ and $R_5$ together are an oxo group. However groups $R_3$ of the form AR are also of interest, especially when $R_4$ is hydrogen and $R_5$ together with $R_6$ is the second bond of a double bond and also when $R_4$ and $R_5$ together are an oxo group. When $R_3$ is a group AR, R is preferably a phenyl group which, as indicated, may optionally be substituted by a halogeno group, for example a bromo, chloro or especially a fluoro group or more particularly a $C_{1-3}$ halogenoalkyl group, for example a propyl, ethyl or especially a methyl group substituted by one, two or especially three halogeno groups, particularly groups as just described. The preferred substituent is a $CF_3$ group, and in general substitution is preferably at the meta position, although the particular preference is for a phenyl group which is unsubstituted.

As indicated, $R_3$ itself or a group R in a group $R_3$ of the form AR may also be an aromatic heterocyclyl group. In general such heterocyclyl groups are of most interest as part of a group AR. In either instance, groups of interest are furyl, pyrrolyl, thienyl, pyridyl, oxazolyl, thiazolyl and pyrimidyl, the 5-membered ring systems being of particular interest, such as thiazolyl, especially pyrrolyl, particularly thienyl, for example thien-2-yl, and most particularly furyl, for example fur-2-yl. Such heterocyclyl groups may be substituted, the preferences being as described for the substituted phenyl groups in a group AR but in general it is preferred that the heterocyclyl groups are unsubstituted.

The divalent aliphatic hydrocarbyl group A may be unsaturated, especially by one double or triple bond, for example being a $—CH_2—C{\equiv}C—$ or especially a $—CH_2—CH{=}CH—$ group. However, straight chain alkylene groups A of the form —(CH₂)ₙ— wherein n is 1 to 4 are of most interest, for example —CH₂—, —CH₂CH₂— and —CH₂CH₂CH₂—. The preferred chain length for A is 1 to 3 carbon atoms, especially 1 or 2 carbon atoms.

A group AR may thus conveniently be a $C_{1-4}$ alkyl group, for example an ethyl or especially a methyl group substituted by a $C_6H_5$ or $CF_3$. $C_6H_4$ group or, to a lesser extent, by a furyl or other unsubstituted aromatic heterocyclyl group as specified above. Groups AR of particular interest are benzyl and 2-phenylethyl and, to a lesser extent, the analogues thereof containing a fur-3-yl or especially a fur-2-yl group in place of the phenyl group.

Examples of specific compounds according to the present invention are those containing a combination of the preferences for $R_1$ to $R_8$ indicated above, for example the compounds in which (1) $R_1$ is $CH_3$, $R_2$ is H, $R_3$ is $C_6H_5CH_2$, $R_4$ and $R_5$ are =O, and $R_6$, $R_7$ and $R_8$ are H (cis-3-benzyl-2-methyl-2,3,3a,4,5,6,7,7a-octahydrobenzo [d]isoxazol-4-one);

(2) is $R_1$ is $CH_3$, $R_2$ is H, $R_3$ is $C_6H_5CH_2$, $R_4$ is H, $R_5$ and $R_6$ are a bond, and $R_7$ and $R_8$ are H (cis-3-benzyl-2-methyl-2,3,3a,6,7,7a-hexahydrobenzo [d]isoxazole);

(3) $R_1$ is $CH_3$, $R_2$ is H, $R_3$ is $C_6H_5CH_2CH_2$, and $R_4$, $R_5$ are =O, and $R_6$, $R_7$ and $R_8$ H (cis-2-methyl-3-(2-phenylethyl)-2,3,3a, 4,5,6,7,7a-octahydrobenzo[d ]isoxazol-4-one);

(4) $R_1$ is $CH_3$, $R_2$ is H, $R_3$ is H, $R_4$ and $R_5$ are =O, and $R_6$, $R_7$ and $R_8$ are H (cis-2-methyl -2,3,3a,4,5,6,7,7a-octahydrobenzo[d]isoxazol-4-one); and (5) $R_1$ is $CH_3$, $R_2$ is H, $R_3$ is H, $R_4$ is H, $R_5$ and $R_6$ are a bond, and $R_7$ and $R_8$ are H (cis-2-methyl-2,3,3a,6,7,7a-hexahydrobenzo[d]isoxazole).

Of these, compound (1) and especially compound (4) are of particular interest.

As indicated, the compounds of formula (I) may exist in the form of an amine type salt formed with a physiologically acceptable inorganic or organic acid. A preferred acid is hydrochloric acid but other acids which may be used include hydrobromic, sulphuric, nitric, phosphoric, isethionic, acetic, fumaric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic acid. In general, however, use of the free base rather than a salt is preferred.

Although the stereochemistry of the molecule is in part indicated in formula (I), a group $R_3$ which is not hydrogen may adopt one of two orientations relative to the two mutually cis hydrogen atoms at positions 3a and 7a. It is preferred, however, that this group has the trans configuration relative to these hydrogen atoms, i.e. the hydrogen atom $R_2$ and the hydrogen atoms at the 3a and 7a positions are similarly disposed in the cis configuration. Thus, the preferred form of each of the specific compounds (1) to (3) hereinbefore may be identified as having the relative stereochemistry 3R*,3aS*, 7aS* (the lowest numbered position, position 3, being assigned the R* configuration). Moreover, it will be appreciated that the compounds according to the invention will be resolvable into enantiomeric forms, one of which may be of particular value by virtue of its level of therapeutic activity and/or physical properties such as greater aqueous solubility, etc.

The compounds of formula (I) may be prepared by a number of alternative routes. In a first process a compound of formula (II) is reacted with a compound of formula (III)

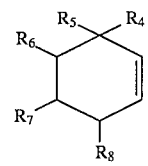

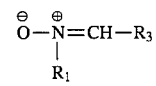

in which $R_1$ to $R_8$ are as defined for the compound of formula (I). Such a process is particularly suited to the preparation of compounds (I) in which $R_1$ is a substituted or unsubstituted aliphatic hydrocarbyl group and $R_3$ is a group AR. The preparation of compounds of formula (I) in which $R_3$ is hydrogen is more conveniently effected through the formation of the compound of formula (III) in situ through the use of a compound of formula (IIIa), $HN(R_1)$-$CH_3$, which is then converted to the compound of formula (III)

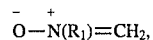

through the use of tungstate catalysed oxidation of the secondary amine (IIIa).

In a second process a compound of formula (II) as defined above is reacted with a compound of formula (IV) and a compound of formula (V)

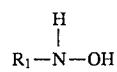

in which $R_1$ and $R_3$ are as defined for the compound of formula (I), the compound of formula (V) often being in salt form. Such a process is of particular value as a route to compounds (I) in which one or both of $R_1$ and $R_3$ is hydrogen.

It will be appreciated, however, that the compounds of formula (I) may also be prepared by modifications of these processes and by other alternative processes which will be apparent from the chemical art.

The first mentioned process generally requires heating of the reactants together, for example at 70°–100° C. in a sealed tube under an inert gas such as nitrogen for a period of 14 to 24 hours. As indicated, the N-oxide may alternatively be generated in situ by oxidation of the corresponding secondary amine, for example with pertungstic acid, when the reaction may be effected at a lower temperature, for example at room temperature. The second mentioned process generally requires reaction in a suitable solvent, for example ethanol, at room temperature, for example for a similar time period to the first mentioned process.

When the compound of formula (I) is in salt form, such salts may be prepared from the free base by treatment with the appropriate acid, either in a polar solvent such as water, if necessary with the application of heat, or more conveniently generating an acid such as hydrochloric acid in situ in a non-aqueous solvent, for example methanol as illustrated in Example 5.

The compounds of formula (I) are of value for the treatment of anxiety, being of particular interest for the treatment of anxiogenesis caused by withdrawal from benzodiazepines such as diazepam as they exhibit cross tolerance with these benzodiazepines in comparison with buspirone, for example, which does not. The compounds (I) are also of interest for the treatment of anxiogenesis caused by abruptly ceasing administration of drugs of abuse and in particular nicotine, alcohol and cocaine.

The compounds of formula (I) are alternatively of value for use in the improvement of learning and/or the reversal of amnesia, for example arising from Alzheimer's disease or vascular dementias.

The dose rates required to achieve effective anxiolysis, improvement in learning ability or reversal of amnesia will of course vary with the mammal treated, the mammal's body weight, surface area, age and general state of health, but as a guide it may be stated that in human patients a suitable dose for parenteral administration is in the range of 0.001 ng/kg to 10 mg/kg, particularly 1 ng/kg to 1 mg/kg, and for oral administration is in the range of 1 μg/kg to 10 mg/kg, particularly 10 μg/kg to 1 mg/kg and especially 10 μg/kg to 100 μg/kg, and that other mammals may be treated on a similar mg/kg basis. Such doses may be repeated as desired, for example 2 to 3 times a day during the period of treatment. Doses outside these ranges may also be given if appropriate. In general the improvement of learning ability and/or the reversal of amnesia requires somewhat lower doses within the ranges given than the treatment of anxiety.

Administration may be by mouth or, less usually, parenterally (including subcutaneously, intramuscularly and intravenously) or topically.

Whilst it is possible for the compound (I) to be administered alone it is preferable to present it in a pharmaceutical composition. Compositions of the present invention for medical use comprise one or more of the active compounds (I) together with one or more pharmaceutically acceptable diluents or carriers and, optionally, other therapeutic ingredients. The diluent(s) or carrier(s) should be pharmaceutically acceptable in the sense of being compatible with the other ingredients of the formulation and not deleterious to the recipient thereof.

Compositions include those suitable for oral, parenteral or topical administration. The formulations may conveniently be presented in unit dosage form and may be prepared by any of the methods well known in the art of pharmacy. In general, formulation includes the step of bringing the active compound(s) (I) into association with a diluent or carrier and, where appropriate, one or more accessory ingredients. Usually, the formulations are prepared by bringing the active compound uniformly and intimately into association with a liquid or with a finely divided solid or with both and then, where appropriate, shaping the product into desired formulations.

Compositions of the present invention suitable for oral administration may conveniently be presented as discrete units such as capsules, cachets, tablets or lozenges, each containing a predetermined amount of the active compound, for example as a powder or granules, or as a solution or a suspension in an aqueous liquid or non-aqueous liquid such as a syrup, an elixir, an emulsion or a draught. The compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Moulded tablets may be made by moulding, in a suitable machine, a mixture of the powdered active compound with any suitable carrier.

A syrup may be made by adding the active compound to a concentrated, aqueous solution of a sugar, for example sucrose, to which may be added any accessory ingredient. Such accessory ingredient(s) may include flavourings, an agent to retard crystallisation of the sugar or an agent to increase the solubility of any other ingredient, such as a polyhydric alcohol, for example glycerol or sorbitol.

Compositions suitable for parental administration conveniently comprise a sterile aqueous preparation of the active compound which is preferably isotonic with the blood of the recipient.

Other types of composition include aerosols and suppositories.

BRIEF DESCRIPTION OF THE DRAWINGS

The invention will now described in more detail with reference to the accompanying drawings, in which.

EXAMPLES

Figure 1:
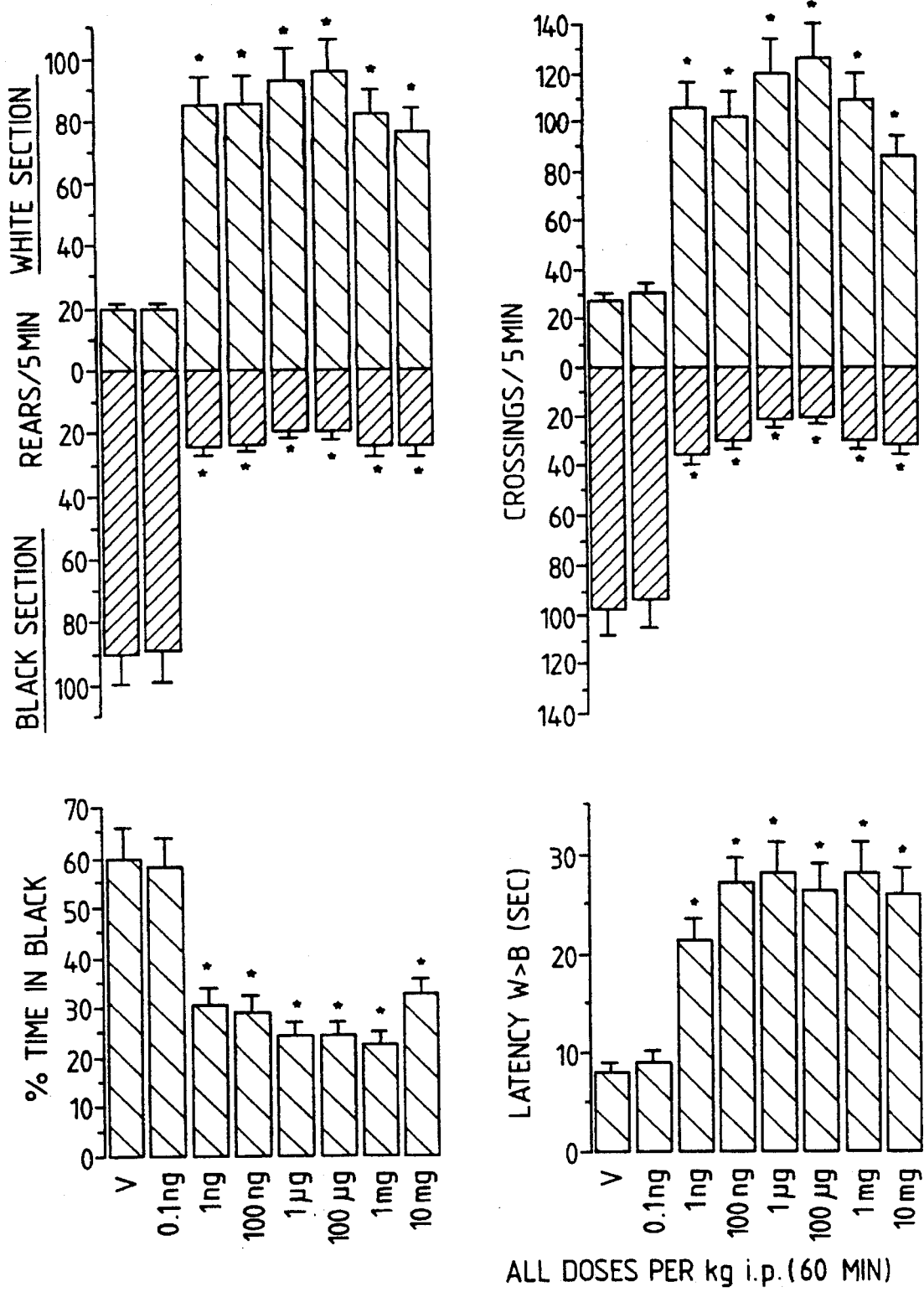
FIGS. 1 and 2 show the results of studies of a compound of the invention on mice in the black: white test box.

The invention is illustrated by the following Examples. The designation rel-(3R*, 3aS*,7aS*) in the names of the compounds of Examples 1, 2, 3, 5 and 6 indicates that the substituent at the 3 position is oppositely orientated relative to the two cis hydrogen atoms at positions 3a and 7a.

Example 1

Preparation of rel,(3R*,3aS*,7aS*)-3-benzyl-2-methyl-2,3,3a,4,5,6,7,7a-octahydrobenzo[d]isoxazol-4-one and substituted derivatives thereof (A)

In a dry sealed tube under $N_2$ were placed N-(2-phenylethylidene)methylamine N-oxide (2.0 g, 13.4 mmol) and 2-cyclohexenone (5 ml). The reagents were stirred at 100° C. for 15 hours. Unreacted 2-cyclohexenone was removed by Kugelrohr distillation to yield the crude product as a viscous brown oil (K100%). The crude product was purified by flash chromatography on silica gel (Sorbsil C60, 60A) using 60:40 v/v petroleum ether (fraction of bp 40°–60° C):ethyl acetate as the solvent system to give the unsubstituted title compound as an orange oil (2.48 g. 75%), $\upsilon_{max}$ (film) 2944, 2872, 1709, 1455, 1238 cm$^{-1}$; $\delta_H$ (250 MHz, CDCl$_3$-Me$_4$Si) 1.75–1.95 (4H, br m), 2.20–2.40 (2H, br m), 2.50 (3H, s), 3.70–3.80 (1H, t), 2.85–2.95 (2H, t), 3.45–3.55 (1H, br m ), 4.30–4.40 (1H, br m ), 7.15–7.30 (5H, br m), M/z 246 ( MH$^+$ 100% ) (Found: MH$^+$ 246.149; C$_{15}$H$_{19}$ NO$_2$ rquires MH$^{30}$ 246.1522).

(B)

rel -(3R*, 3aS*, 7aS*)-3-Benzyl -2-methyl -2,3,3a, 4,5, 6,7,7a-octahydrobenzo[d]isoxazol-4-one [2.51 g, 102 mMol; prepared as described under (A)] in methanol was stirred at 0° C. and treated dropwise with acetyl chloride (0.73 ml, 102 mMol). The solvents were removed in vacuo to yield an oil which became a white foam under high vacuum (0.01 mm Hg). This crude product was recrystallised from acetone to give the unsubstituted title compound hydrochloride as a white crystalline solid, m.p. 154°–156° C. (decomposition) in quantitative yield.

(C)

N-(2-m-Fluorophenylethylidene)methylamino N-oxide (1.0 g, 4.61 mmol) and 2-cyclohexenone (0.5 g, 5.20 mmol) were refluxed in toluene overnight under nitrogen. Removal of the solvent gave rel -(3R*, 3aS*, 7aS*)-3-m-fluorobenzyl -2-methyl 2,3,3a,4,5,6,7,7a-octahydrobenzo[d]isoxazol-4-one as a brown oil (341 mg, 24%), $\delta_H$ (400 MHz, CDCl$_3$-Me$_4$Si) 1.98–2.30 (6H, m), 2.52 (3H, s), 2.72 (1H, m), 2.95–2.98 (2H, br m), 3.51 (1H, br m), 4.40 (1H, br m), 7.41–7.52 (4H, m); $\delta_C$ (100 MHz, CDCl$_3$-Me$_4$Si) 19.70, 25.97, 29.70, 39.43, 40.54, 45.01, 59.16, 69.62, 76.70, 123.50, 125.47,126.32, 128.82, 133.06, 138.82; M/z 314 [(M+H)$^+$ 12%](Found: M$^+$ 313.1285; C$_{16}$H$_{18}$NO$_2$F$_3$ requires M$^+$ 313.1290).

(D)

The procedure described in (C) was repeated using N-[2-(m-trifluoromethylphenyl)ethylidene]methylamine N-oxide in place of N-(2-m-fluorophenylethylidene)methylamine N-oxide to provide rel-(3R*, 3aS*, 7aS*) -3-m-(trifluoromethyl)benzyl -2-methyl 2,3a 4,5,6,7,7a-octahydrobenzo[d]isoxazol -4-one as an oil, $\delta_H$ (400 MHz, CDCl$_3$-Me$_4$Si) 1.73–1.84 (6H, m), 2.32–2.36 (1H, m), 2.42 (3H, s), 2.51–2.64 (1H, br m), 2.73–2.80 (1H, br m), 3.38 (1H, br s), 4.27 (1H, br s), 6.77–7.16 (4H, m); $\delta_C$ (100 MHz, CDCl$_3$-Me$_4$Si) 19.36, 25.65, 40.11, 58.71, 69.32, 76.25, 112.95, 113.17, 116.03, 116.25, 125.01, 129.43, 129.52, 140.20, 208.86; M/z 264 [(M+H)$^+$ 18%](Found: M$^+$ 263.1324; C$_{15}$H$_{18}$NO$_2$F requires M$^+$ 263.1322).

EXAMPLE 2

Preparation of rel-(3R*,3aS*,7aS*)-3-benzyl-2-methyl-2,3,3a,6,7,7a-hexahydrobenzo[d]isoxazole N-(2-Phenylethylidene)methylamine N-oxide (797 mg, 5.34 mmol) and 1,3-cyclohexadiene (3 ml) were heated together at 70° C. in a sealed tube under nitrogen for 14 hours. The solution was cooled to room temperature and the excess 1,3-cyclohexadiene was removed under reduced pressure to yield a viscous oil (1.07 g, 87%). This crude product was purified by flash chromatography using 60:40 v/v petroleum ether (fraction of bp 40°–60° C.):ethyl acetate as the solvent system to give the title compound (Rf=0.34) as a pale yellow oil (375 mg, 35%), $\upsilon_{max}$ (film) 3030, 2920, 2840, 1605, 1495, 1455, 1090 cm$^{-1}$; $\delta_H$ (400 MHz; CDCl$_3$-Me$_4$Si) 1.80–2.00 (4H, br m), 2.20–2.25 (1H, m), 2.60–2.65 (3H, s), 2.75–2.95 (2H and 1H, m), 4.20–4.25 (1H, br), 5.6–6.0 (2H, br m), 7.20–7.30 (5H, br m); M/z 229 (MH$^+$ 100%) (Found: MH$^+$ 230.1545; C$_{15}$H$_{19}$NO requires MH$^+$ 230.1574).

EXAMPLE 3

Preparation of rel-(3R*,3aS*, 7aS*)-2-methyl-3-(2-phenylethyl)-2,3,3a,4,5,6,7, 7a-octahydrobenzo[d]isoxazol-4-one N-(3-Phenylpropylidene)methylamine N-oxide (1.50 g, 9.19 mmol) and 2-cyclohexenone (5 ml) were heated at 80°–90° C. for 24 hours in a sealed tube under nitrogen. The solution was cooled to room temperature and the excess 2-cyclohexenone was removed under reduced pressure using Kugelrohr distillation to yield the crude product as a dark yellow oil (2.36 g, 99%). The crude product was purified by flash chromatography using 60:40 v/v light petroleum (fraction of bp 40°–60° C.):ethyl acetate as the solvent system to give the title compound as a colourless oil (2.11 g, 89%), $\upsilon_{max}$ (film) 2941, 2872, 1710, 1454, 1235 cm$^{-1}$; $\upsilon$H (250 MHz, CDCl$_3$–Me$_4$Si) 1.70–2.0 (6H, br m), 2.25–2.55 (2H, m), 2.60–2.80 (2H, m), 2.70 (3H, s), 2.75 (1H, t), 3.25 (1H, br m), 4.45 (1H, br m), 7.10–7.30 (5H, br m) ; M/z 259 (M$^+$ 100%) (Found: M$^+$ 259.1572; C$_{16}$H$_{21}$NO$_2$ requires M$^+$ 259.1603).

EXAMPLE 4

Preparation of Cis-2-methyl-2,3,3a,4,4a,5,6,7,7a-octahydrobenzo[d]isoxazol-4-one (A)

A mixture of sodium acetate trihydrate (13.6 g, 0.1 mmol ), aqueous formaldehyde (37% w/w) (10.0 ml, 0.13 mol ) and 2-cyclohexenone (10.6 g, 0.11 mol) in ethanol (80 ml) was vigorously stirred. To this was added over 90 minutes N-methyl hydroxylamine hydrochloride (8.6 g, 0.1 mol) in ethanol (45 ml) containing water (2.5 ml), and the stirring was continued overnight. The reaction mixture was then filtered, condensed to half volume under reduced pressure and then neutralised using saturated sodium bicarbonate solution. The aqueous solution was extracted using ethyl acetate (3×75 ml). The combined organic extracts were washed with water (1×30 ml) and dried using saturated sodium chloride solution (1×50 ml) and magnesium sulphate. Removal of the solvents in vacuo gave a crude product in the form of a pale yellow oil (9.18 g, 59%). 5.3 g of this crude product was purified by flash chromatography using ethyl acetate as the solvent system to give the title compound as a colourless oil (6.86 mg), $\upsilon_{max}$ (film) 3419, 2951 2872 1709 1671 1456, 1239, 1087 cm$^{-1}$; $\delta_H$ (250 MHz, CDCl$_3$-Me$_4$Si) 1.90–2.05 (4H, br m), 2.35–2.50 (2H, m), 2.70 (3H, s), 2.80–3.20 (2H and 1H, br m), 4.40–4.70 (1H, m); M/z 156 (MH$^+$ 100%).

(B)

In a variation of the procedure described under (A) of Example 1 the title compound was alternatively prepared by the reaction of N-(ethylidene)methylamine N-oxide with 2-cyclohexenone. The N-oxide is formed in situ by the tungstate catalysed oxidation of dimethylamine (Na$_2$WO$_4$.2H$_2$O/H$_2$O$_2$/ (CH$_3$)$_2$NH in a 1.4:77:35 molar ratio in H$_2$O) and reacted for 12 hours at room temperature with a 1.05 molar excess of the 2-cyclohexenone. working up by extraction with CH$_2$Cl$_2$, washing with H$_2$O, saturated aqueous NaHCO$_3$ and saturated brine, and evaporation gives a brown oil which is purified by flash chromatography as described under (A) above to give the title compound with similar properties to those described under (A) above.

EXAMPLE 5

Preparation of rel-(3R*,3aS*,7aS*)-3-benzyl-2-methyl 2,3,3a, 4,5,6,7,7a-octahydrobenzo[d]isoxazole N-(2-phenylethylidene)methylamine N-oxide (5.0 g, 33.5 mmol) and cyclohexene (15 ml) were heated at 80° C. for 18 hours in a sealed tube under nitrogen. The solution was cooled to room temperature and the cyclohexene was removed under reduced pressure to yield a viscous brown oil (6.5 g, 84%). The crude product was dissolved in hot either (50 ml) and refrigerated. After standing for 48 hours the product was filtered to give the title compound as a white crystalline solid, (1.15 g, 15%). Two further crops were isolated from the washings, (2.37 g, 31%) and (2.05 g, 27%) but these were less pure than the main fraction.

Note

The crude product was alternatively purified by flash chromatography using 60:40 v/v light petroleum (fraction of bp 40°–60° C.):ethyl acetate to give the title compound ($R_f$=0.31).

EXAMPLE 6

Preparation of rel-(3R,3aS*,7aS*)-3-fur-2-yl-2-methyl-2,3,3a, 4,5,6,7, 7a-octahydrobenzo[d]isoxazol -4-one N-(Fufurylidene)methylamine N-oxide (1.03 g, 9.44 mmol) and 2-cyclohexenone (3 ml) were heated at 90° C. for 1 hour. After cooling to room temperature hydroquinone (22 mg) was added and the temperature raised to 65°–70° C. for 11 hours. The solution was cooled and the excess 2-cyclohexenone was removed by Kugelrohr distillation under reduced pressure to yield a light brown oil (1 .88 g, 90%). The crude product was purified by flash chromatography using ethyl acetate:petroleum ether (bp 40°–60° C.) in a ratio of 3:7 v/v as the solvent system. The title compound had an Rf of 0.29 and was isolated as a pale yellow oil (1.36 g, 65%), $\upsilon_{max}$ (thin film) 2957, 2877, 1710, 1248, 1011 cm$^{-1}$; δH (400 MHz, CDCl$_3$-Me$_4$Si) 1.67–2.00 (4H, m), 2.34–2.38 (1H, m), 2.44–2.49 (1H, m), 2.67 (3H, s), 3.28–3.31 (1H, t), 4.20 (1H, br s), 4.67–4.68 (1H, br s), 6.27–6.30 (2H, m), 7.34–7.35 (1H, t); M/z 222 ( MH$^+$ 100%).

EXAMPLE 7

Tests of Physiological Activity Drugs

The compound of Example 1(A) (hereinafter identified as SP1640) was suspended in a minimum quantity of polyethylene glycol (PEG) and diluted with distilled water. Ondansetron, zacopride, nicotine dihydrogen tartrate, cocaine hydrochloride and scopolamine hydrobromide were dissolved in saline. Alcohol was made up as an 8% w/v solution of ethanol in drinking water. Diazepam was dissolved in the minimum quantity PEG and made up to volume with distilled water. All drugs were administered in a volume of 1 ml/kg (rat) and 1 ml/100 g (mouse).

(1) Anxiolytic Activity

The compound of Example 1(A) was tested for anxiolytic activity using the following procedures.

Studies Using the Black:White Box Test

Naive BKW male albino mice (Bradford bred) 30–35 g were used in all studies. 10 mice were normally housed in each cage and kept for at least two weeks on a 12 hour light/dark cycle with lights off at 07.00 h. Behavioural testing was conducted between 13.00–18.00h in a darkened room illuminated with red light. Nice were taken from the dark holding room to the testing room in an enclosed trolley and allowed at least 1 hour for adaptation to the new environment.

The apparatus used for the detection of changes in exploratory behaviour consisted of an open-topped box (45×27×27 cm high) lined into 9 cm squares, two-fifths painted black and Illuminated under a dim red light (1×60 W) and partitioned from the remainder of the box which was painted white and brightly illuminated with a 60 W light source located 17 cm above the box. An opening 7.5×7.5 cm located at floor level in the centre of the partition allowed access between the two compartments. At the start of testing mice were placed individually into the centre of the white, brightly lit area of the test box.

The mice were observed over a 5 minute period by remote video recording and four behaviours noted: (i) the number of exploratory rearings in the white and black sections, (ii) the number of line crossings in the white and black areas, (iii) the time spent in the white and black areas and (iv) the latency of the initial movement from the white to the black area. An anxiolytic effect is evidenced by an enhanced preference for the white area as compared with the black area which is that preferred under normal conditions.

In initial studies, separate groups of naive mice received the vehicle only or SP1640 at 1 ng/kg, 1 μg/kg or 1 mg/kg i.p. 60 minutes before exposure to the black:white test box. A second study determine a wider dose range (0.1 ng/kg–10 mg/kg). In subsequent studies the oral efficacy of SP1640 was determined over a wide dose range (0.01 ng/kg–1 mg/kg).

Mice were used once only in treatment groups of 5. Results were analysed using single factor ANOVA followed by Dunnett's t-test for comparing multiple treatments with a single control.

Studies on Rat Social Interaction

Adult male Hooded-Lister rats (Bradford bred) 225–275 g were housed in groups of five and kept on a 12 hour light/dark cycle with lights on at 07.00 h. Tests were conducted between 13.00–18.00 h in an illuminated room following a period of adaptation.

The apparatus used for the detection of changes in rat social interaction and exploratory behaviour consisted of an open-topped perspex box (51×51×20 cm high) with 17×17 cm areas marked on the floor of the box. Two naive rats, from separate housing cages, were placed into the box (with 2×60 W bright white illumination above) and their behaviour observed over a 10 minute period by remote video recording. Two behaviours were noted (i) social interaction between the animals was determined by timing (s) sniffing of partner, crawling under or climbing over partner, genital investigation of partner, following partner and (ii) exploratory locomotion was measured as the number of crossings of the lines marked on the floor of the test box.

Separate groups of rats received vehicle or SP1640 (0.1 ng/kg–10 mg/kg i.p.) 40 minutes before testing.

Naive animals were used once only in drug treated pairs in treatment groups of 6–8 pairs. Data obtained were analysed using single factor ANOVA followed by Dunnett's t-test.

Maintenance of Effects on Long-Term Treatment And Consequences of Withdrawing from Long-Term Treatment These studies used the mouse black:white box. Mice received SP1640 1 ng/kg i.p. b.d. or 1 mg/kg i.p. b.d. for 14 days and the treatments were abruptly withdrawn.

Separate groups of mice were tested on days 3, 7 and 14 of treatment and then 8, 12, 24, 48 and 96 hours after the last dose.

Mice were used on one occasion only in groups of 5. Data obtained were analysed using single factor ANOVA and Dunnett's t-test where appropriate.

Assessment of Ability to Cross-Tolerate with Diazepam

These studies used the mouse black:white box model. Mice were treated with diazepam 10 mg/kg i.p. b.d. for 7 days and the treatment was then abruptly withdrawn. The withdrawal phenomena which characteristically result following the abrupt cessation of diazepam treatment are maximal 24 hours after the last dose of diazepam. SP1640 (1 μg/kg i.p. b.d.) was given to separate groups of mice during the period of withdrawal to determine the ability to prevent the development of withdrawal phenomena.

Mice were used on one occasion only in groups of 5. Data obtained were analysed using single factor ANOVA and Dunnett's t-test where appropriate.

Ability to Inhibit the Behavioural Consequences of Withdrawing From Drugs of Abuse Following long-term treatment of mice with alcohol (8% w/v in the drinking water for 14 days), nicotine (0.1 mg/kg i.p. b.d. for 7 days) or cocaine (1 mg/kg i.p. b.d. for 14 days) and abrupt withdrawal of treatment, mice (tested in the black:white box) exhibited marked behavioural changes which were maximal. 24 hours after cessation of treatment. The ability of SP1640 to prevent the development of these behavioural changes was determined when SP1640 1 μg/kg i.p. b.d. was given to mice during the 24 hour period of withdrawal, the last dose 40 minutes prior to behavioural testing.

Mice were used once only in treatment groups of 5. Data obtained were analysed using single factor ANOVA and Dunnett's t-test where appropriate.

RESULTS

The results obtained in the various tests for anxiolytic activity were as follows.

Studies in the Black:White Test Box

In initial studies SP1640 was administered to mice via the intraperitoneal route at a dose of 1 ng/kg, 1 μg/kg or 1 mg/kg. SP1640 produced changes in behaviour indicative of an anxiolytic potential at 1 ng/kg, 1 μg/kg and 1 mg/kg. In a second study using a dose range of 0.1 ng/kg to 10 mg/kg SP1640 produced changes in behaviour indicative of anxiolysis over the range of 1 ng/kg–10 mg/kg. The results of the second study are set forth in FIG. 1 (in this and subsequent figures the symbol V (vehicle) or the symbol C (control) indicate the control in which only the vehicle was used without compound).

In subsequent experiments the oral efficacy of SP1640 was established and full 1 dose response curves constructed.

Figure 2:
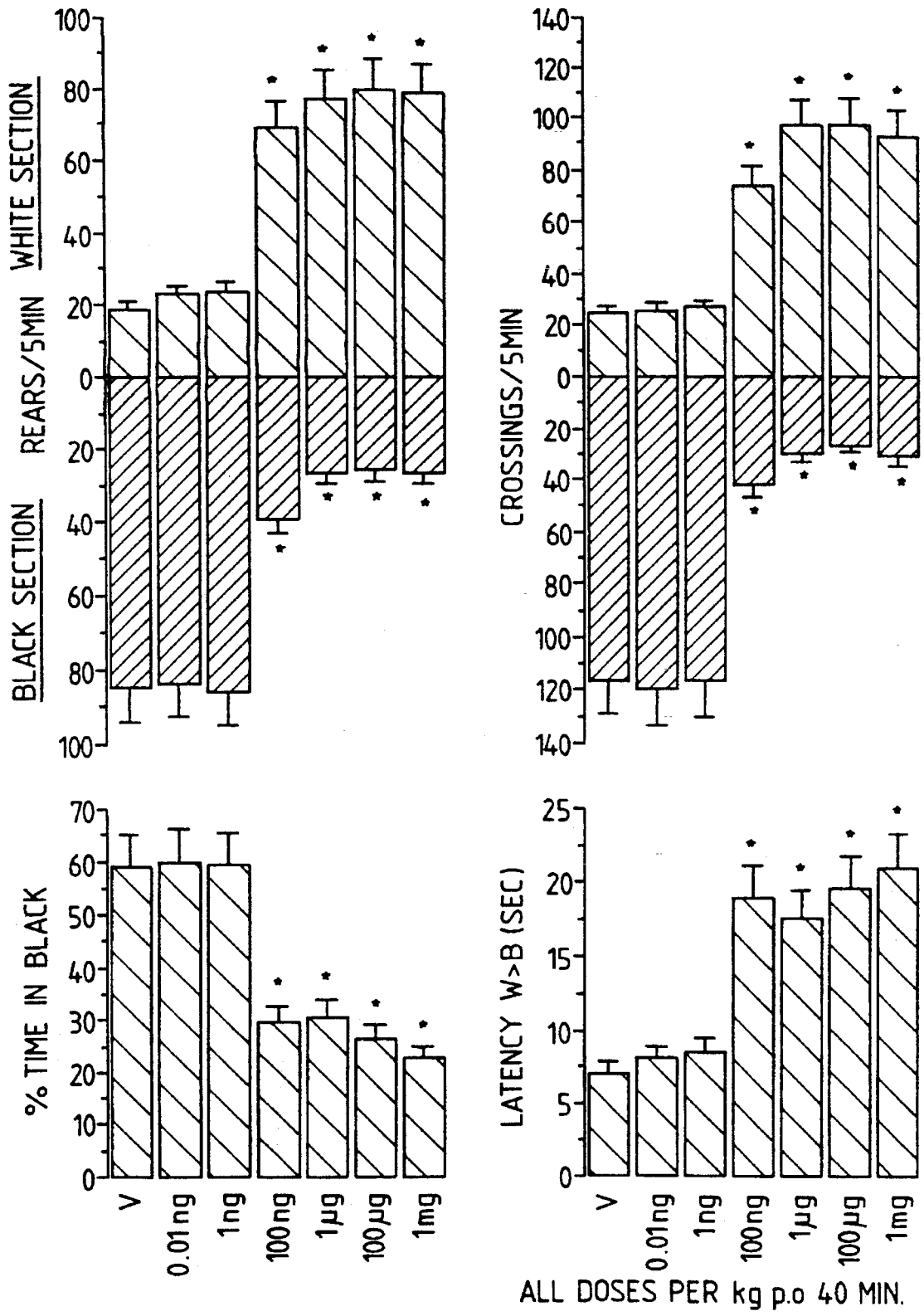

SP1640 was effective to induce anxiolysis following oral administration over a wide dose range (100 ng/kg–1 mg/kg). The results are set forth in FIG. 2.

At none of the doses of SP1640 tested was there any suggestion of the development of sedation.

Studies on Rat Social Interaction

Figure 3:
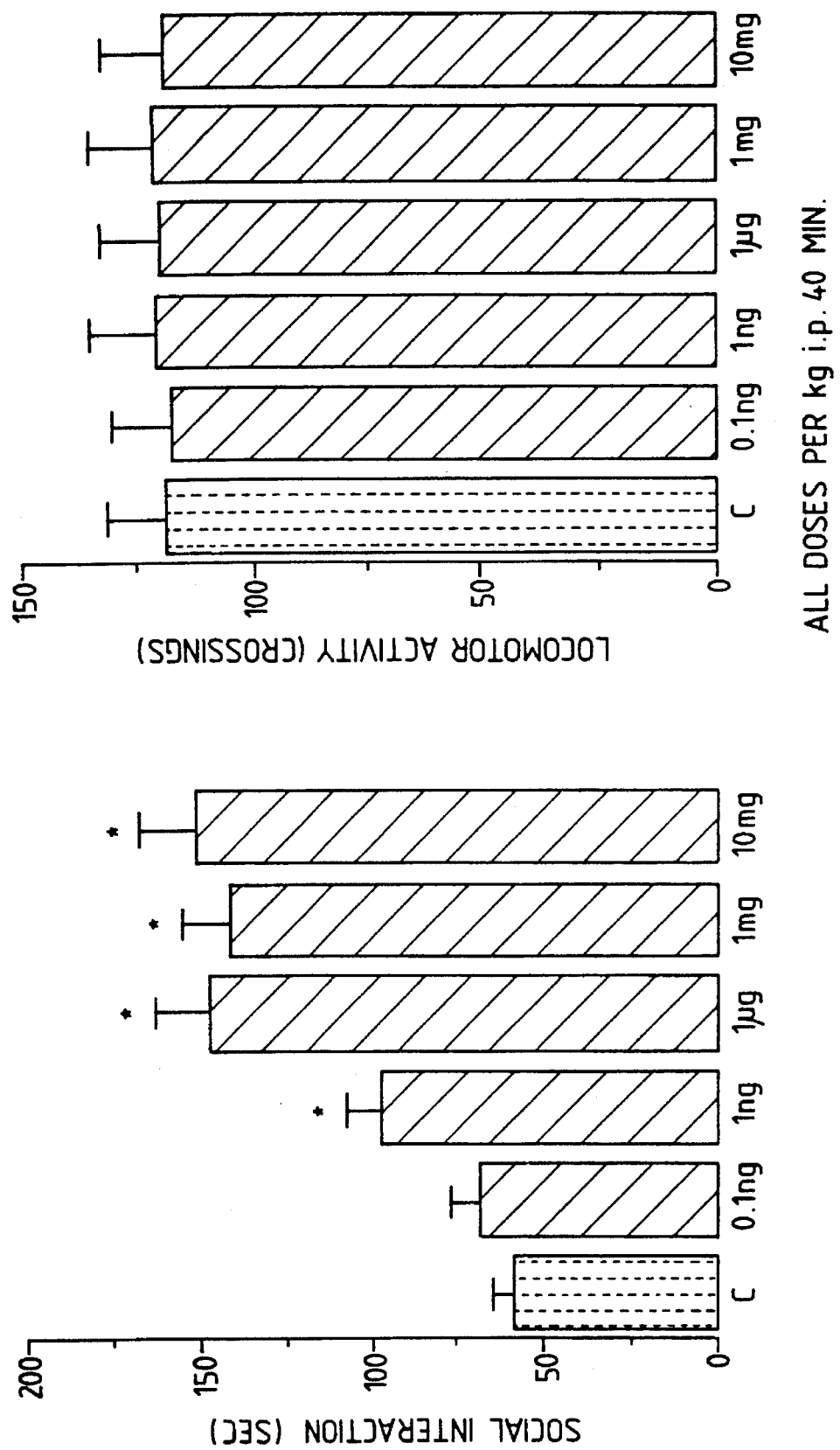
FIG. 3 shows the results of studies of a compound of the invention on rat social interaction.

SP1640 was administered intraperitoneally at doses of 0.1–10 mg/kg. SP1640 increased rat social interaction at 1 ng/kg–10 mg/kg (FIG. 3). SP1640 did not cause changes in locomotor activity at any of the doses tested. The results are set forth in FIG. 3.

Figure 4:
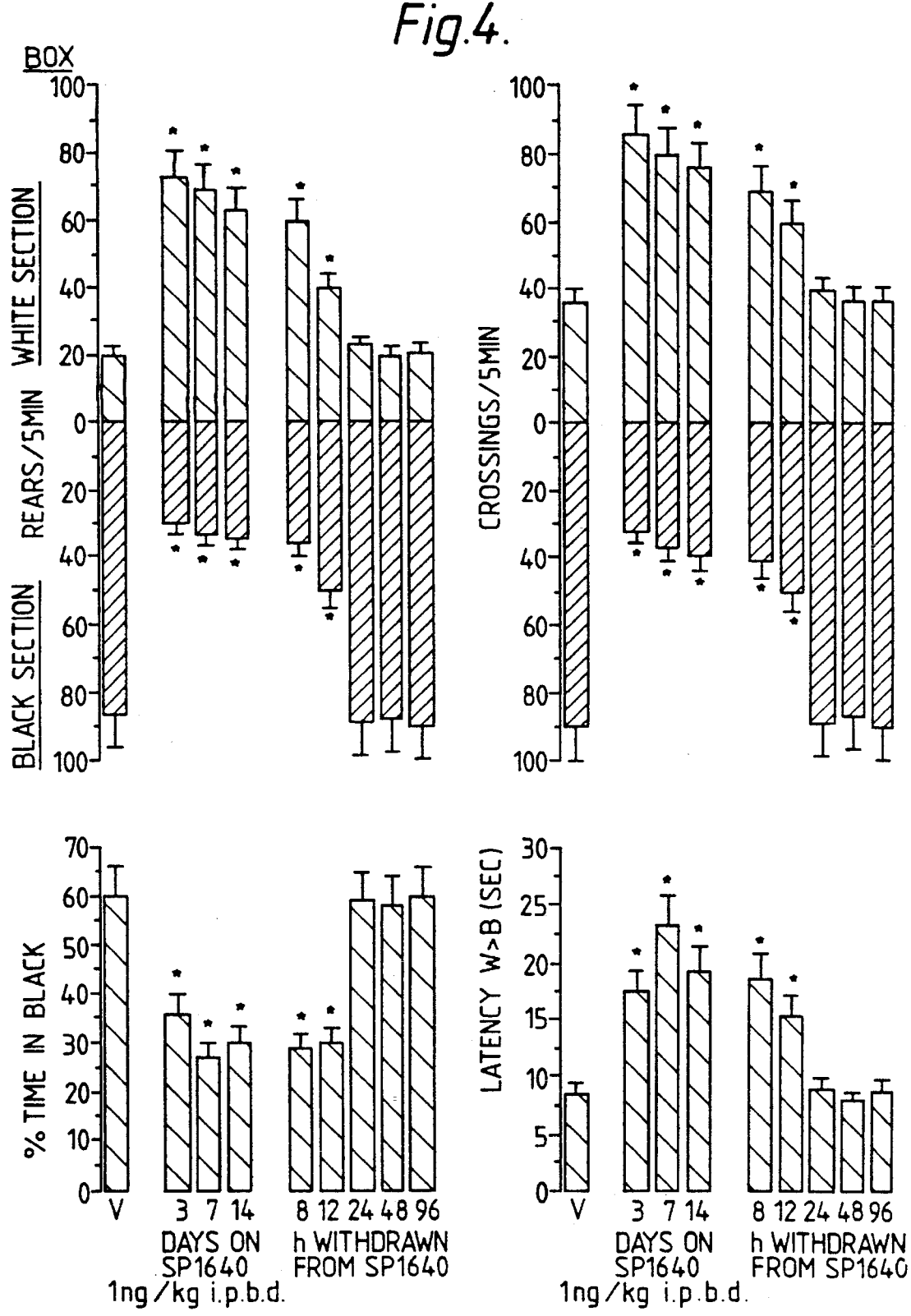
FIGS. 4 and 5 show the results of a compound of the invention on the anxiolytic profile over different periods of time.
Figure 5:
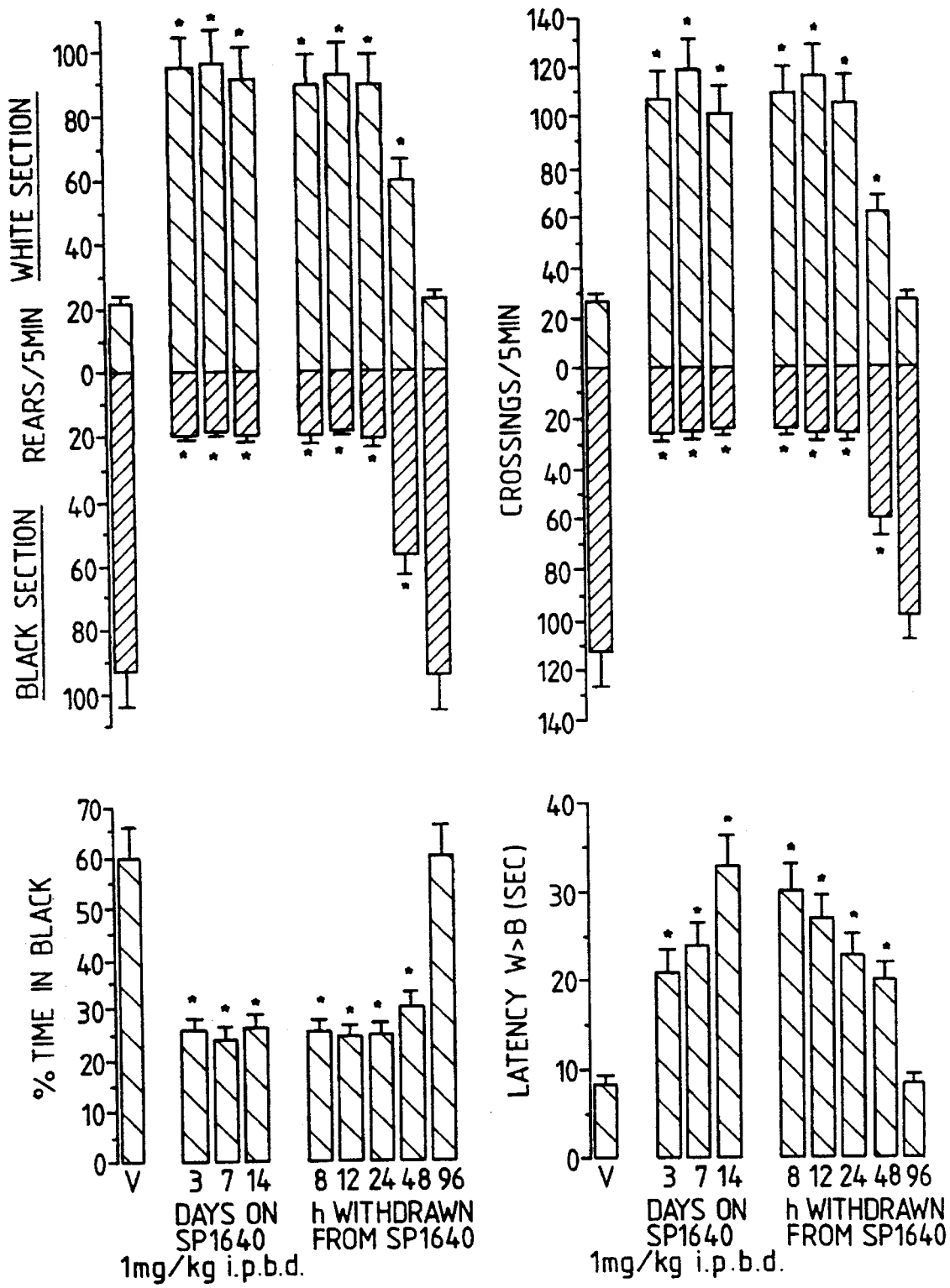

Maintenance of Effects on Long-Term Treatment and Consequences of Withdrawing From Long-Term Treatment During long-term treatment with SP1640 (1 ng/kg i.p. b.d. and 1 mg/kg i.p. b.d.) the anxiolytic profile of responding was maintained when tested on days 3, 7 and 14 of treatment, the results being set forth in FIGS. 4 and 5. Following abrupt cessation of treatment there was no indication of the development of anxiogenesis; rather, the anxiolytic profile was maintained for up to 12 hours (SP1640 1 ng/kg, FIG. 4) or 48 hours (SP1640 1 mg/kg, FIG. 5).

Assessment of Ability to Cross-Tolerate with Diazepam

Figure 6:
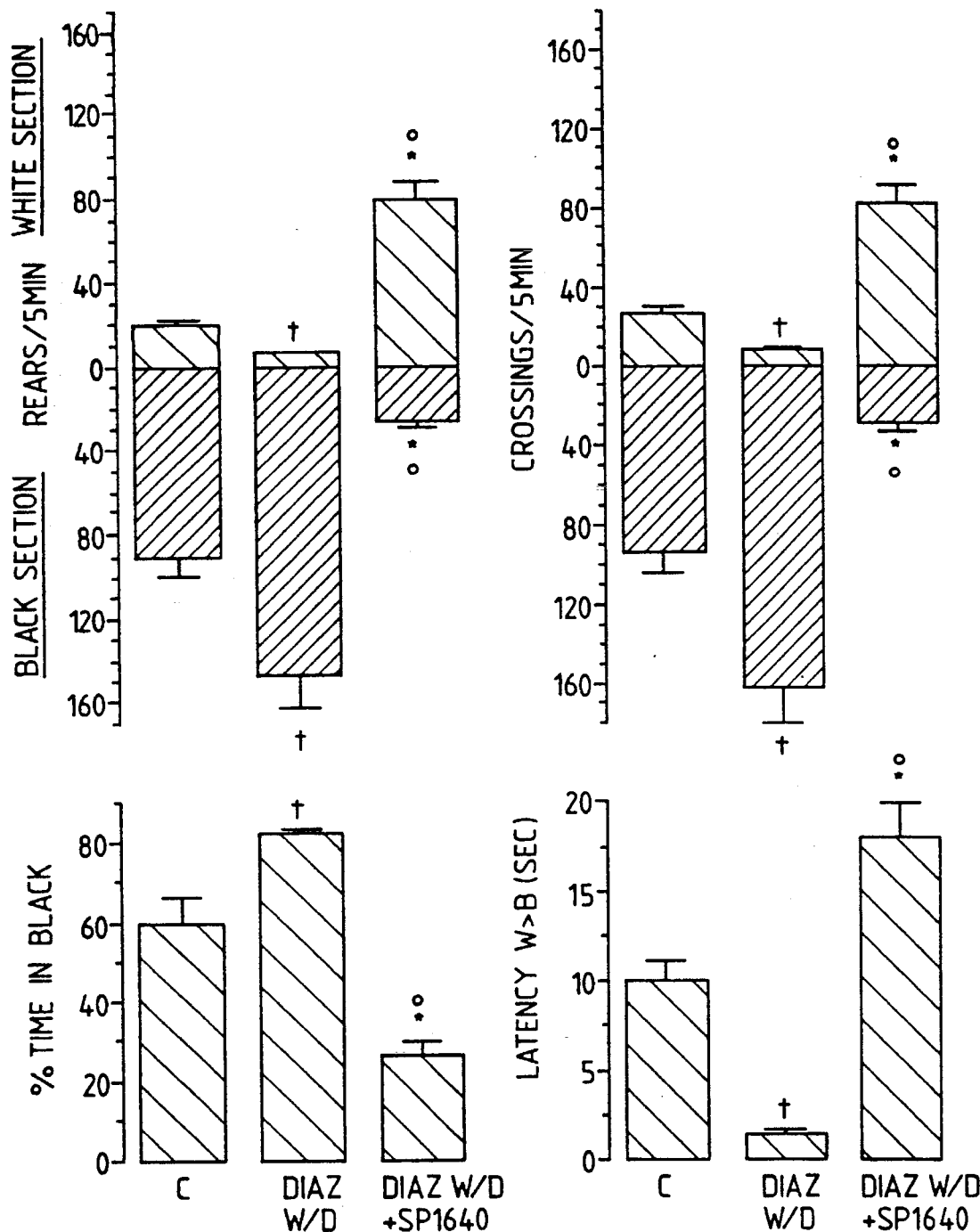
FIG. 6 shows the results of studies to assess the ability to cross-tolerate with diazepam.

The anxiolytic effect of diazepam given for 7 days is seen from FIG. 6. 24 hours after cessation of treatment the anxiolytic profile had reversed to an anxiogenic profile of responding.

SP1640 (1 μg/kg i.p. b.d.) given during the period of withdrawal prevented the development of withdrawal anxiogenesis and induced an anxiolytic profile of responding. The results produced are set forth in FIG. 6.

Ability to Inhibit the Behavioural Consequences of Withdrawing From Drugs of Abuse Alcohol (8% w/v) in drinking water for 14 days induces behavioural changes indicative of anxiolysis, within 24 hours of withdrawing alcohol from the drinking water mice displayed a profile of activity indicative of anxiogenesis.

Figure 7:
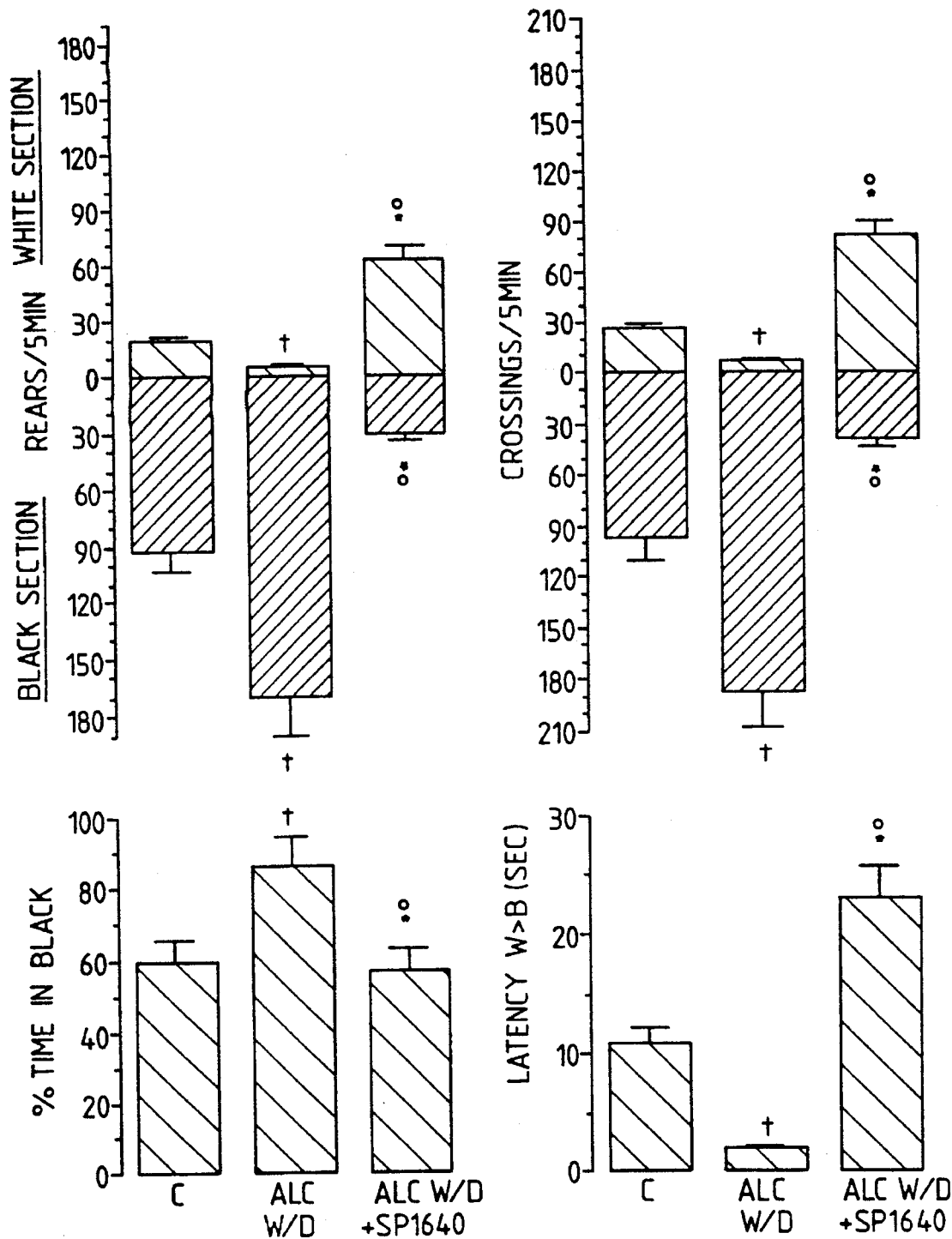
FIGS. 7 through 9 show the results of studies on the ability to inhibit behavioral consequences of withdrawal from drugs of abuse.

SP1640 (1 μg/kg i.p.) prevented the development of withdrawal anxiogenesis. The results are set forth in FIG. 7.

Figure 8:
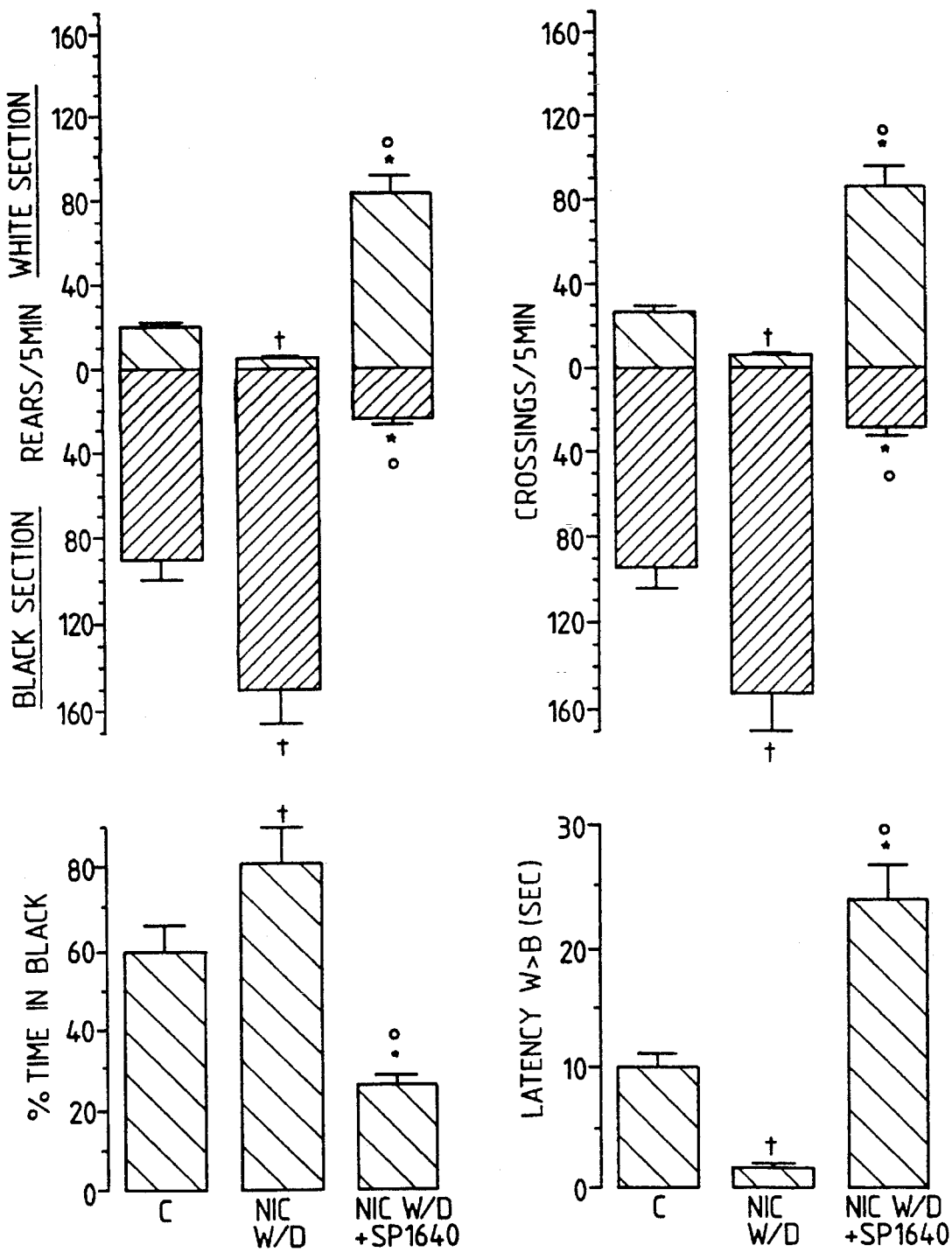

Nicotine (0.1 mg/kg i.p. b.d.), administered for 7 days, also induced behavioural changes indicative of anxiolysis. Within 24 hours of withdrawing nicotine treatment profile of activity indicative of anxiogenesis was apparent. SP1640 (1 μg/kg i.p. b.d.) prevented the development of withdrawal phenomena when given during the period of withdrawal. The results are set forth in FIG. 8.

In a similar way to alcohol and nicotine, cocaine (1mg/kg i.p. b.d.), administered for 14 days, produced changes in responding indicative of anxiolysis which, following a 24 hour period of withdrawal, reverted to a profile of anxiogenesis.

Figure 9:
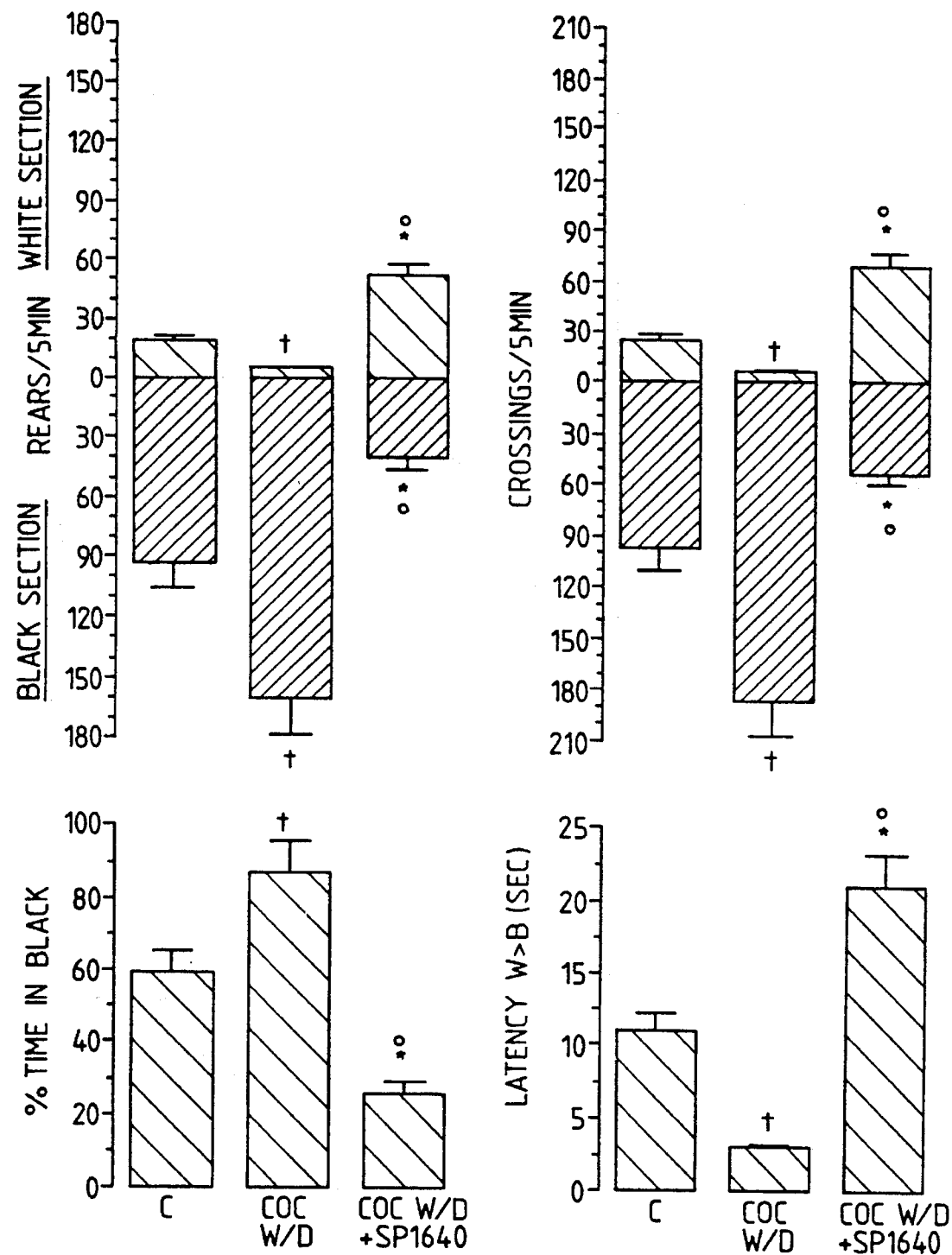

SP1640 (1 μg/kg i.p. b.d.) prevented the development of withdrawal phenomena when given during the period of withdrawal. The results are set forth in FIG. 9.

(2) Improvement of Learning and Reversal of Scopolamine-Induced Amnesia

The compound of Example 1(A) (SP1640) was tested at sub anxiolytic doses.

The following procedure was employed:

Mouse Habituation Test

The studies used male albino (BKW) mice initially weighing 27–35 g (young adult mice of 6–8 weeks) or 40–45 g (aged mice of 9 months). In their home room mice were housed in groups of 10 and were given free access to food and water. The mice were kept at a 12 hour light and 12 hour dark cycle with lights off at 7.00 a.m. and on at 7.00 p.m.

The test apparatus consisted of an open-topped box (45× 27×27 cm) one third painted black and illuminated under a dim red light (1×60W) and partitioned from the remainder of the box which was brightly illuminated with a 100 W light source located 17 cm above the box. Access between these two areas was enabled by means of a 7.5×7.5 cm opening located at floor level in the centre of the partition (which also served to prevent diffusion of light between the two compartments of the test box). The floor area was lined into 9 cm squares.

The habituation test was carried out daily by placing mice in the centre of the white section of the test box (mice taken from dark home environment in a dark container, to the experimental room maintained in low red lighting, and would normally be averse to the bright white conditions). Testing was carried out between 8.30 a.m. and 12.30 p.m. The test period was 5 minutes per day. Behaviour was assessed via remote video recording, and the following measurements taken:

1. Latency to move from the white to the black section (sec).
2. Numbers of exploratory rears in the white and black sections during the 5 minute tests.
3. Numbers of line crossings (exploratory locomotion) in the white and black sections during the 5 minute test.
4. % Time spent in the black section of the box during the 5 minute test.
5. Numbers of transitions between the black and white sections of the test box during the 5 minute test (since this parameter was not changed in any situation in the present studies, data for transitions is not given or commented on further).

On repeated daily exposure to the box young adult mice habituate to the test situation by moving rapidly into the black area where they spend most time and exhibit most behaviour (measured as exploratory rears and crossings of lines marked on the test box floor). Generally, for young adult mice the habituation process occurs over a 4–6 day period and, for example latency for the initial movement from the white to the black section is reduced from initial values of 10–12 seconds to 1–4 seconds by the 5th-6th day of test.

In the contrast to the findings with young adult mice (6–8 weeks old), aged mice (9 months old) fail to habituate to the black:white test system. From the first day of test aged animals' behaviour appears to be equally distributed between the white and black sections, and expected changes in behaviour to favour the preferred black environment do not occur.

The habituation profile of young mice was disrupted by acute scopolamine (0.25 mg/kg i.p., 40 minutes before test) (dose carefully selected as minimally effective, without interference from peripheral effects as checked by assessments of the actions of the same dose of methylscopolamine). Aged mice were found to be particularly sensitive to scopolamine and they were challenged with the maximally tolerated dose of 0.1 mg/kg (40 minutes before test). SP1640 was given i.p. b.d. throughout the habituation period (dose of 0.1 ng selected as not interfering with anxiety response). Injections of the compound were at 8.00 a.m. (40 minutes before testing) and 6.00 p.m.

Figure 10:
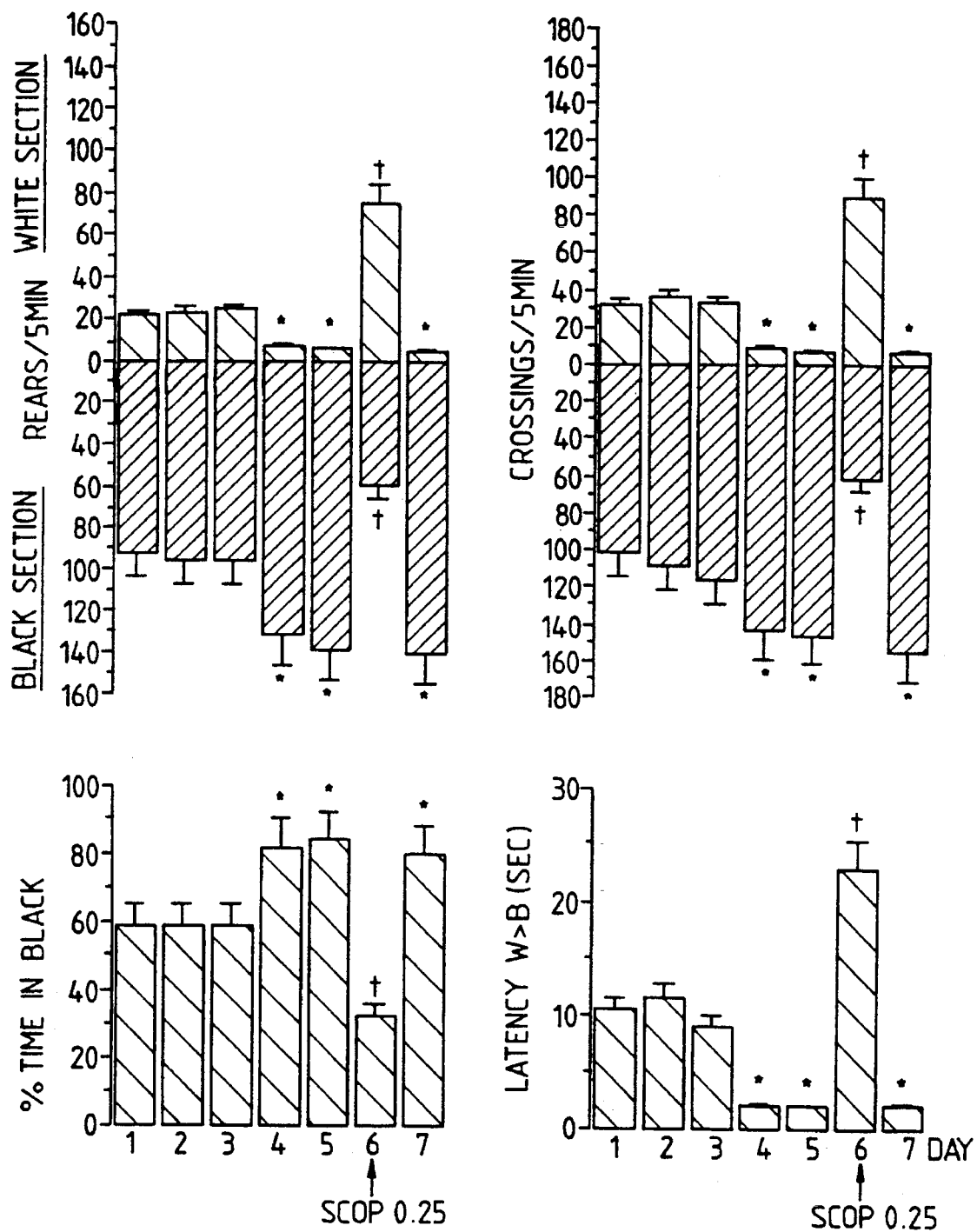
FIGS. 10 through 16 show the results in the mouse habituation test to demonstrate improvement of learning ability and reversal of scopolamine-induced amnesia.
Figure 11:
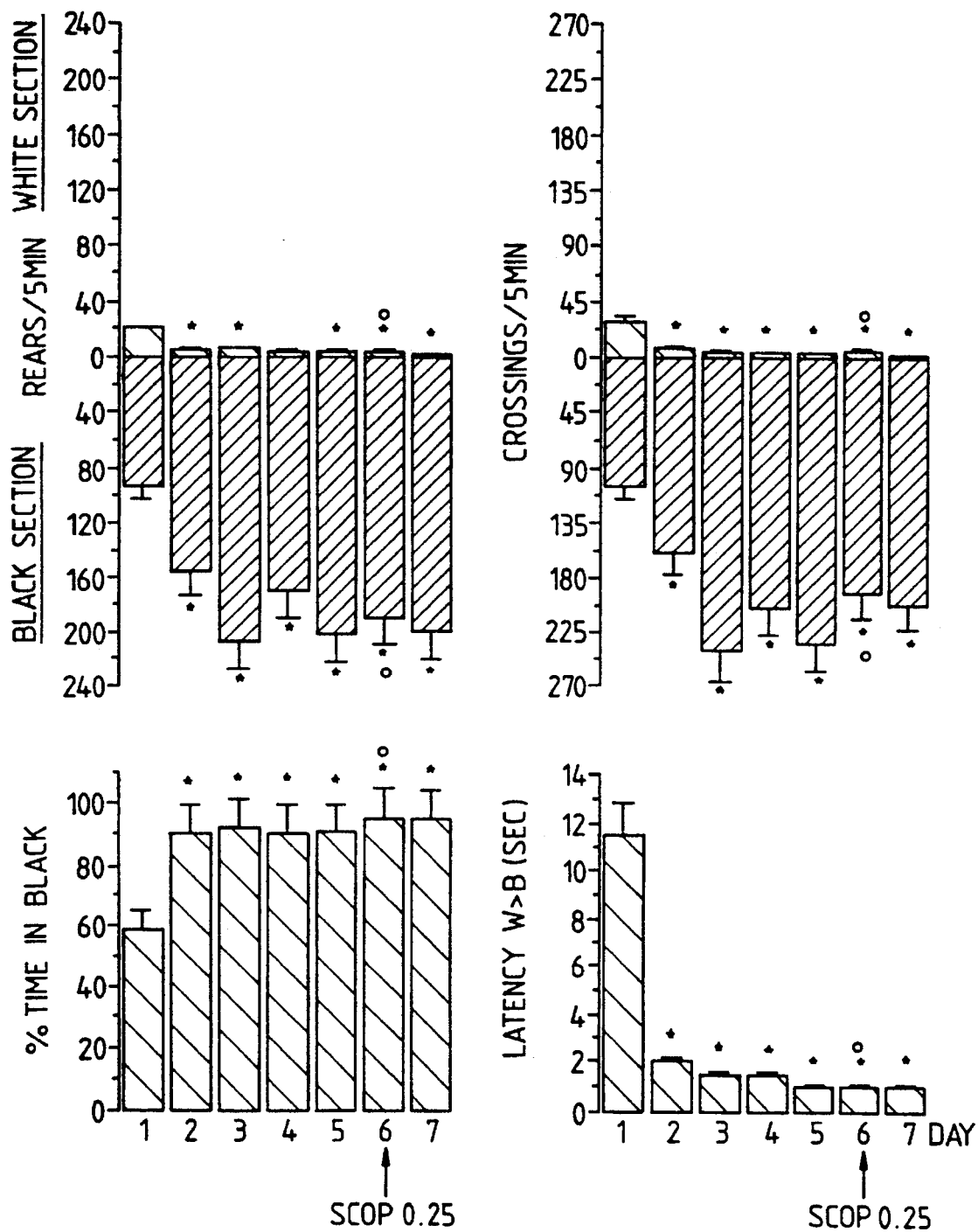
Figure 12:
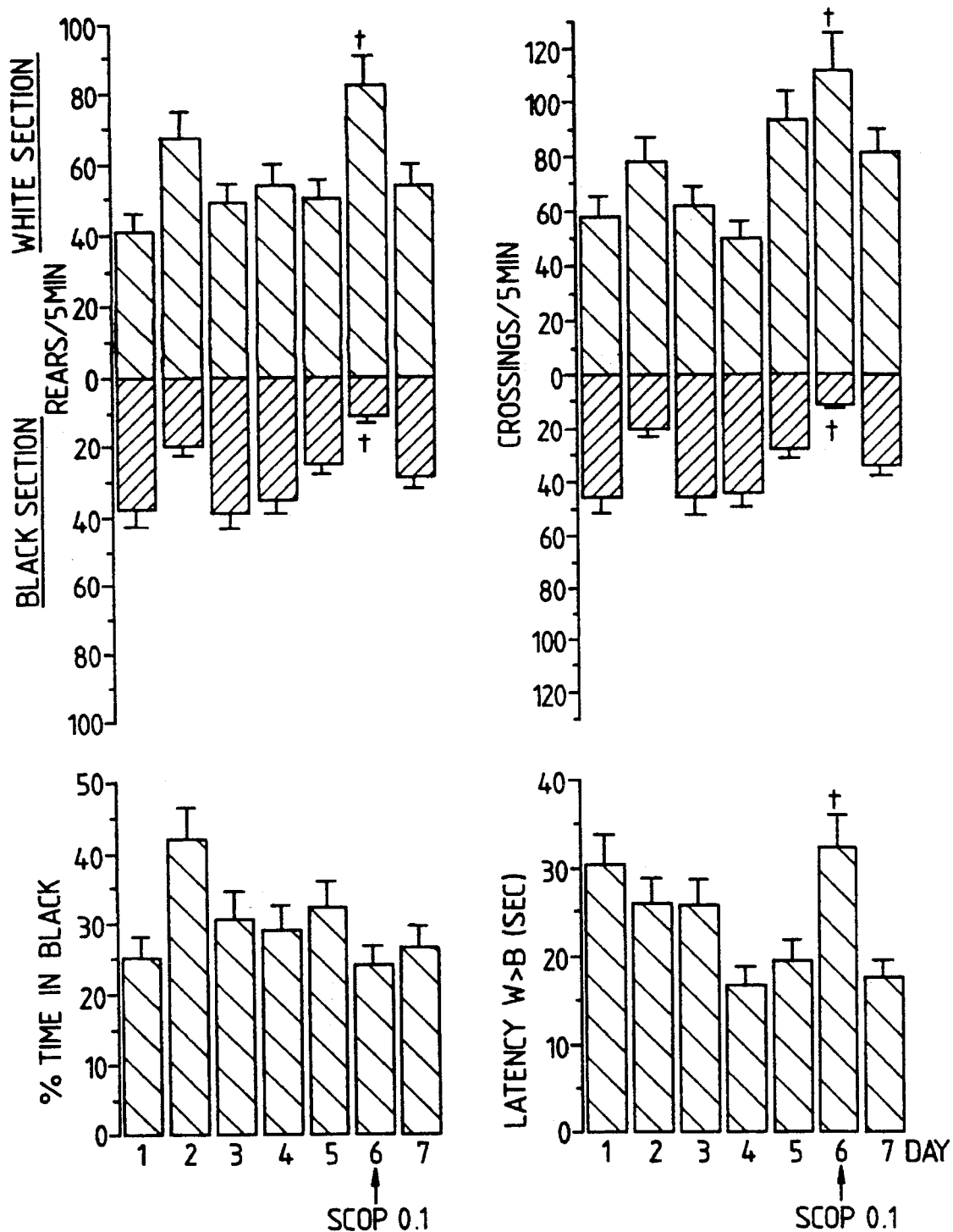
Figure 13:
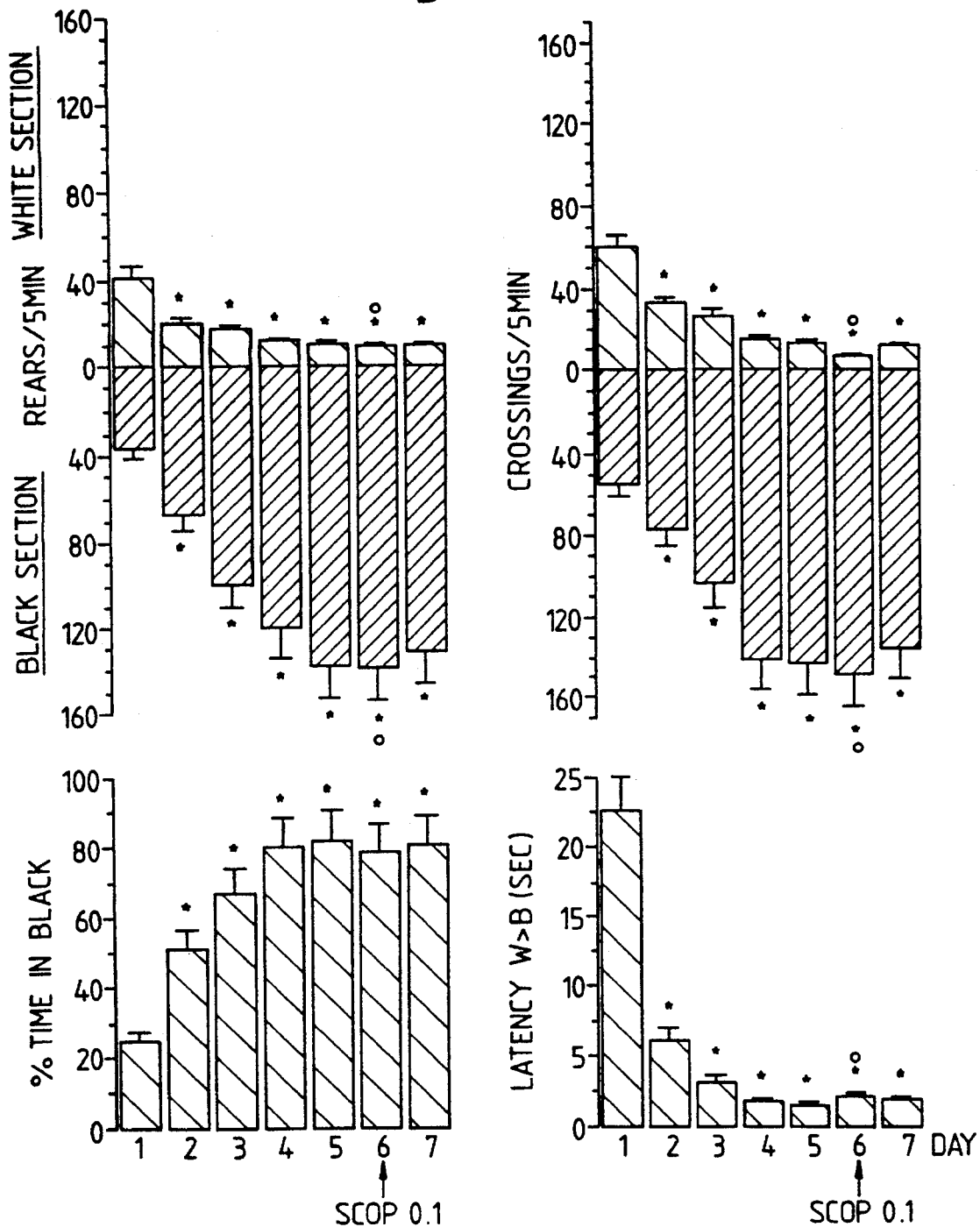
Figure 14:
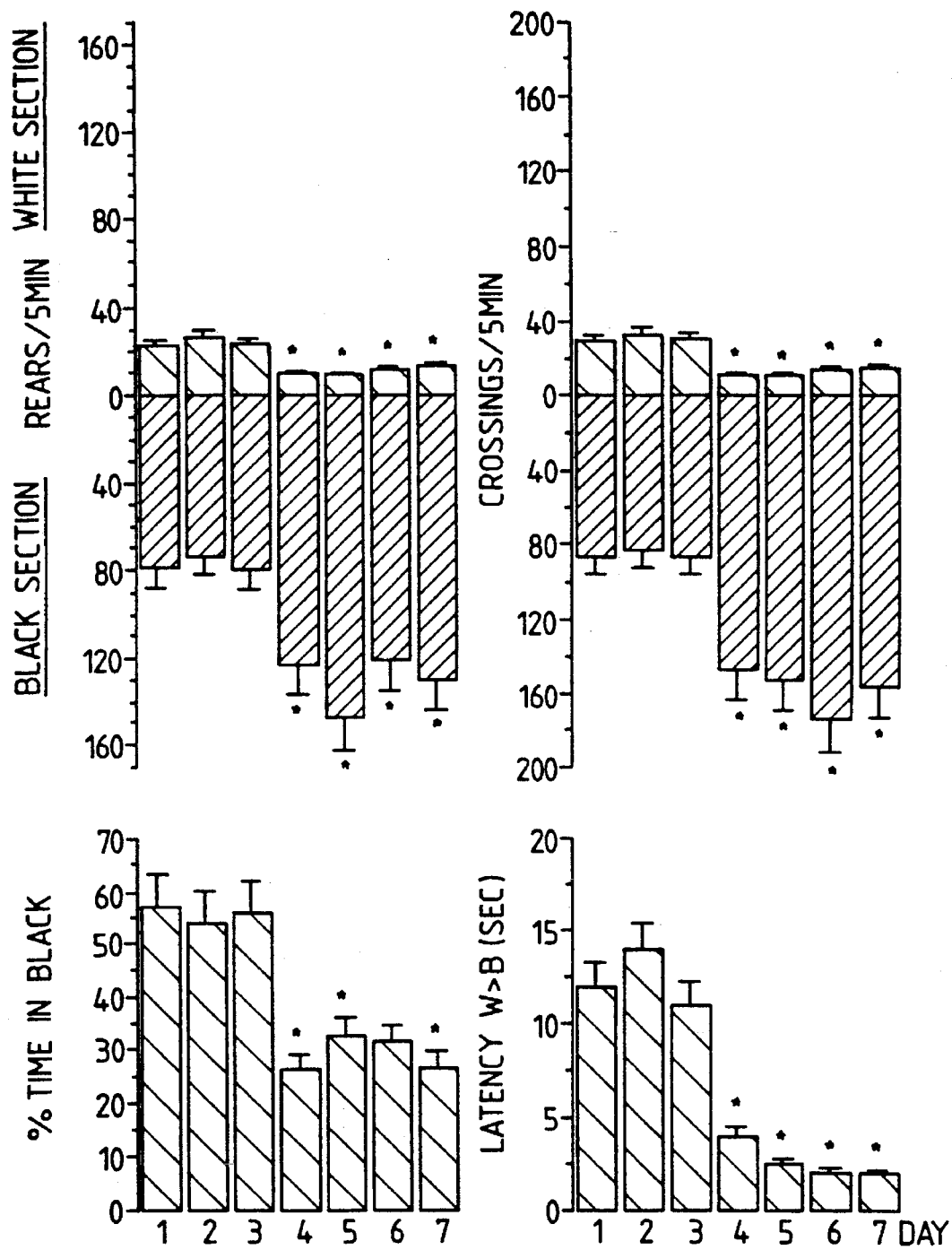
Figure 15:
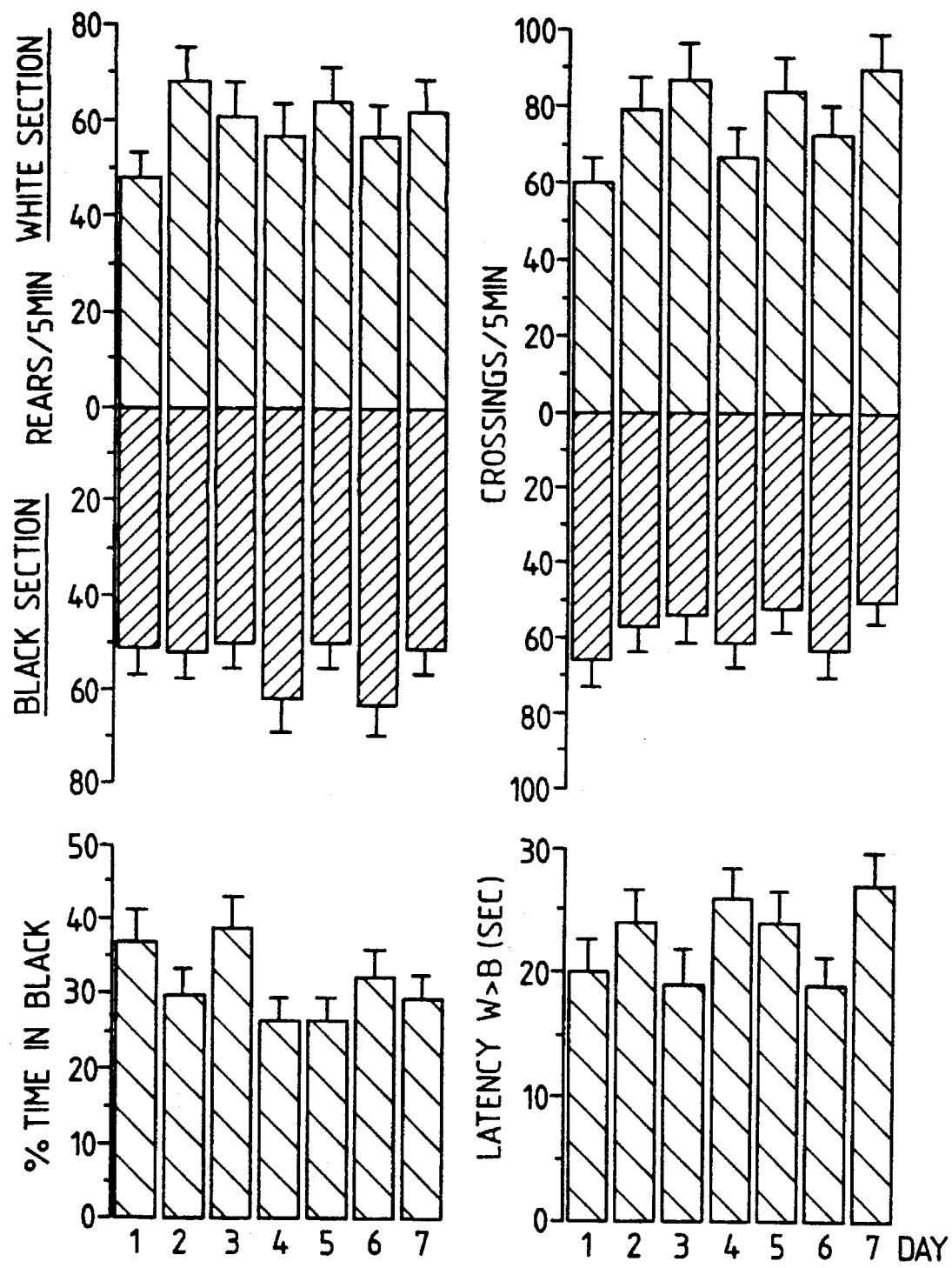
Figure 16:
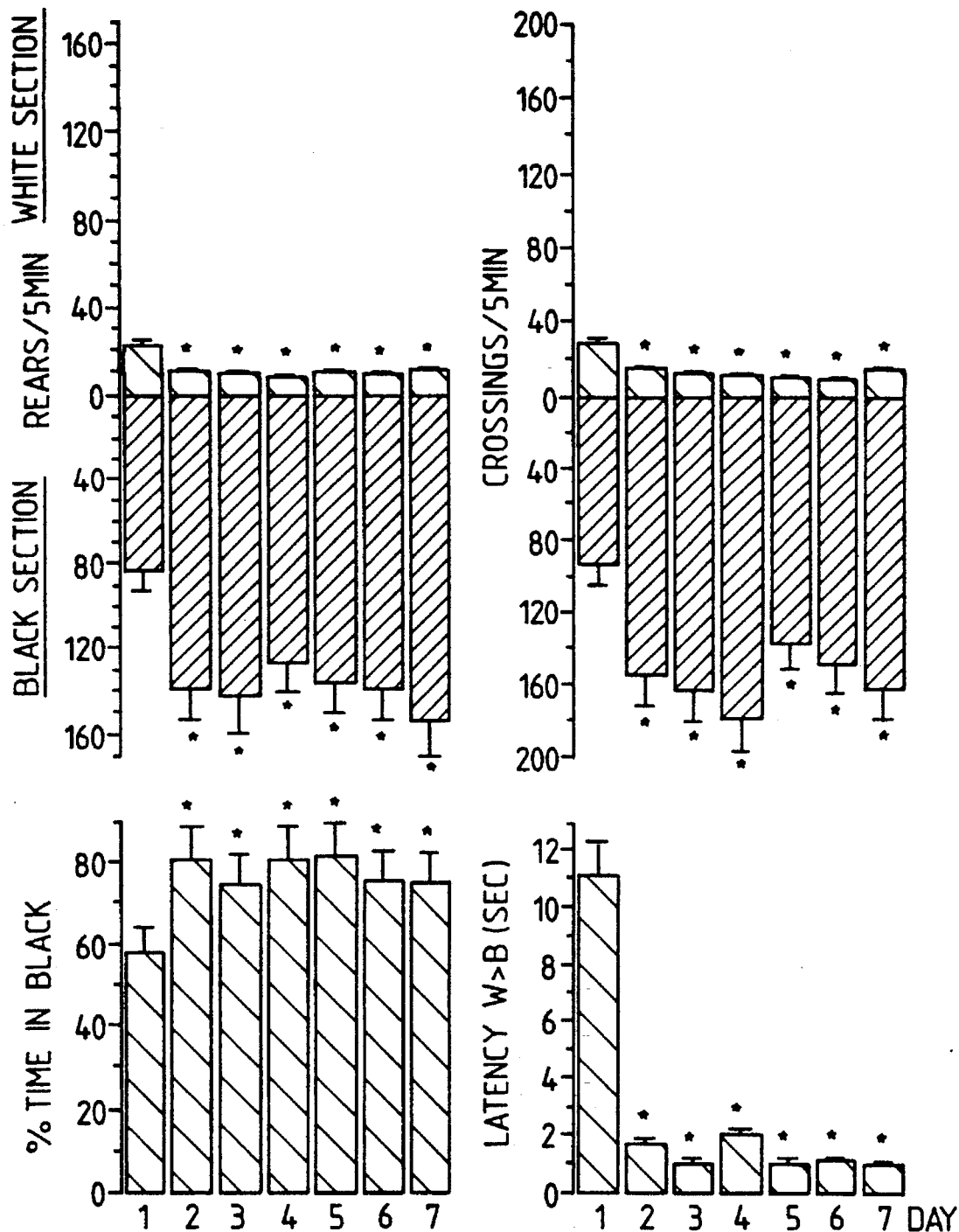

The results are set forth in FIGS. 10 to 16 of which FIGS. 10 and 11 illustrate the ability of SP1640 to improve basal inhibition in young adult mice (FIG. 10 being the control), FIGS. 12 and 13 illustrate the ability of SP1640 to improve basal inhibition in aged mice (FIG. 12 being the control), and FIGS. 14, 15 and 16 illustrate the ability of SP1640 to prevent the impairment in habituation caused by the acute or chronic scopolamine challenge (FIGS. 14 and 15 being the controls).

We claim:

1. A method of treatment of a patient requiring improvement of learning disability and/or reversal of amnesia which comprises administering to said patient a therapeutically effective amount of a compound of formula (I)

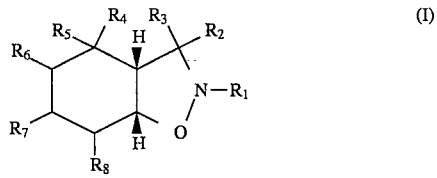

in which $R_1$ represents hydrogen, a $C_{1-6}$ aliphatic hydrocarbyl group or a $C_{1-4}$ aliphatic hydrocarbyl group substituted by a $C_{3-6}$ alicyclic hydrocarbyl group or by a phenyl group, which phenyl group is unsubstituted or substituted by a halogeno or $C_{1-3}$ halogenoalkyl group, $R_2$, represents hydrogen, $R_3$ represents hydrogen, a 5- or 6-membered ring aromatic heterocyclyl group containing one or two heteroatoms selected from nitrogen, oxygen and sulphur which is unsubstituted or substituted by a halogeno or $C_{1-3}$ halogenoalkyl group, or a group AR wherein A is a straight chain $C_{1-4}$ aliphatic hydrocarbyl group terminally substituted by R which is hydrogen, a phenyl group or a 5- or 6-membered ring aromatic heterocyclyl group containing one or two heteroatoms selected from nitrogen, oxygen and sulphur, which phenyl or heterocyclyl group R is unsubstituted or substituted by a halogeno or $C_{1-3}$ halogenoalkyl group, $R_4$ and $R_5$ each represent hydrogen or together represent an oxo group and $R_6$, $R_7$ and $R_8$ each represent hydrogen, or $R_4$ represents hydrogen arid two of $R_5$, $R_6$, $R_7$ and $R_8$ together represent the second bond of a double bond joining positions 4 and 5, 5 and 5 or 6 and 7 with the remaining two of $R_5$, $R_6$, R7 and $R_8$ representing hydrogen, the compound optionally being in the form of a salt thereof formed with a physiologically acceptable inorganic or organic acid.

2. A method for the treatment of a patient requiring improvement of learning disability and/or reversal of amnesia which comprises administering to said patient a therapeutically effective amount of a compound of the formula (I)

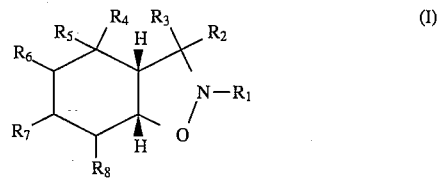

in which $R_1$ represents hydrogen, a $C_{1-6}$ aliphatic hydrocarbyl group or a $C_{1-4}$ aliphatic hydrocarbyl group substituted by a $C_{3-6}$ alicyclic hydrocarbyl group, $R_2$ represents hydrogen, $R_3$ represents hydrogen or a group AR wherein A is a straight chain $C_{1-4}$ aliphatic hydrocarbyl group terminally substituted by R which is hydrogen or a phenyl group which is unsubstituted or substituted by a trifluoromethyl group, $R_4$ and $R_5$ each represent hydrogen or together represent an oxo group and $R_6$, $R_7$ and $R_8$ each represent hydrogen, or $R_4$ represents hydrogen and two of $R_5$, $R_6$, $R_7$ and $R_8$ together represent the second bond of a double bond joining positions 4 and 5, 5 and 5 or 6 and 7 with the remaining two of $R_5$, $R_6$, $R_7$ and $R_8$ representing hydrogen, the compound optionally being in the form of a salt thereof formed with a physiologically acceptable inorganic or organic acid.

3. A method according to claim 3, in which $R_1$ is a $C_{1-6}$ alkyl group.

4. A method according to claim 2, in which $R_1$ is methyl.

5. A method according to claim 2, in which $R_3$ is hydrogen.

6. A method according to claim 2, in which $R_3$ is $C_{1-4}$ alkyl group.

7. A method according to claim 2, in which $R_3$ is a $C_{1-4}$ alkyl group substituted by an unsubstituted phenyl group.

8. A method according to claim 2, in which $R_3$ is a benzyl or 2-phenylethyl group.

9. A method according to claim 2, in which $R_4$ to $R_8$ are each hydrogen.

10. A method according to claim 2, in which $R_4$, $R_7$ and $R_8$ are each hydrogen and $R_5$ and $R_6$ are the second bond of a double bond joining positions 4 and 5.

11. A method according to claim 2, in which $R_4$ and $R_5$ are an oxo group and $R_6$, $R_7$ and $R_8$ are each hydrogen.

12. A method according to claim 2, wherein the compound of formula (I) is cis-2-methyl-2, 3, 3a, 4, 5, 6, 7, 7a-octahydrobenzo[d]benzoisooxazol-4-one.

13. A method according to claim 2 wherein the compound of formula (I) is cis-2-methyl-2, 3, 3a, 6, 7, 7a-hexahydrobenzo[d]isoxazole.

14. A method according to claim 2 wherein the compound of formula (I) is cis-3-benzyl-2-methyl-2, 3, 3a, 4, 5, 6, 7, 7a-octahydrobenzo[d]isooxazol-4-one.

15. A method according to claim 2 wherein the compound of formula (I) is cis-3-benzyl-2-methyl-2, 3, 3a, 6, 7, 7a-hexahydrobenzo[d]isoxazole.

16. A method according to claim 2 wherein the compound of formula (I) is cis-2-methyl-3-(2-phenylethyl)-2, 3, 4, 5, 6, 7, 7a-octahydrobenzo[d]isoxazol-4one.

17. A method according to claim 2, in which a group $R_3$ which is not hydrogen is in the trans configuration relative to the hydrogen atoms at positions 3a and 7a.

18. A method according to claim 14, in which a group $R_3$ which is not hydrogen is in the trans configuration relative to the hydrogen atoms at positions 3a and 7a.

19. A method according to claim 15, in which a group $R_3$ which is not hydrogen is in the trans configuration relative to the hydrogen atoms at positions 3a and 7a.

20. A method according to claim 16, in which a group $R_3$ which is not hydrogen is in the trans configuration relative to the hydrogen atoms at positions 3a and 7a.

* * * * *